United States Patent
Matsushika et al.

(10) Patent No.: US 8,445,243 B2
(45) Date of Patent: May 21, 2013

(54) HEXOSE-PENTOSE COFERMENTING YEAST HAVING EXCELLENT XYLOSE FERMENTABILITY AND METHOD FOR HIGHLY EFFICIENTLY PRODUCING ETHANOL USING THE SAME

(75) Inventors: Akinori Matsushika, Hiroshima (JP); Shigeki Sawayama, Hiroshima (JP); Hiroyuki Inoue, Hiroshima (JP); Keisuke Makino, Kyoto (JP); Tsutomu Kodaki, Kyoto (JP); Seiya Watanabe, Kyoto (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 219 days.

(21) Appl. No.: 12/864,360

(22) PCT Filed: Jan. 22, 2009

(86) PCT No.: PCT/JP2009/050929
§ 371 (c)(1),
(2), (4) Date: Jul. 23, 2010

(87) PCT Pub. No.: WO2009/093630
PCT Pub. Date: Jul. 30, 2009

(65) Prior Publication Data
US 2011/0027847 A1    Feb. 3, 2011

(30) Foreign Application Priority Data

Jan. 24, 2008  (JP) .................................. 2008-014080
Aug. 20, 2008  (JP) .................................. 2008-211274

(51) Int. Cl.
*C12P 7/06*    (2006.01)
*C12N 1/14*    (2006.01)

(52) U.S. Cl.
USPC ........................................ 435/161; 435/255.1

(58) Field of Classification Search
USPC ........................................................ 435/161
See application file for complete search history.

(56) References Cited

U.S. PATENT DOCUMENTS 5,789,210 A    8/1998  Ho et al.
7,226,735 B2 *  6/2007  Jeffries et al. ................ 435/6.18

FOREIGN PATENT DOCUMENTS

| EP | 0 450 430 | 10/1991 |
| JP | 62-65679 | 3/1987 |
| JP | 2008 193935 | 8/2008 |
| WO | 95 13362 | 5/1995 |

OTHER PUBLICATIONS

Information Offer Form by Third Parties issued Feb. 28, 2012 in Japanese patent application No. 2008-211274.
Nancy W.Y. Ho, et al., "Successful Design and Development of Genetically Engineered *Saccharomyces* Yeasts for Effective Cofermentation of Glucose and Xylose from Cellulosic Biomass to Fuel Ethanol", Advances in Biochemical Engineering/Biotechnology, vol. 65, 1999, pp. 163-192.
Anna Eliasson, et al., "Anaerobic Xylose Fermentation by Recombinant *Saccharomyces cerevisiae* Carrying XYL1, XYL2, and XKS1 in Mineral Medium Chemostat Cultures", Applied and Environmental Microbiology, vol. 66, No. 8, Aug. 2000, pp. 3381-3386.
Seiya Watanabe, et al., "Ethanol production from xylose by recombinant *Saccharomyces cerevisiae* expressing protein engineered NADP-dependentxylitol dehydrogenase", Journal of Biotechnology, vol. 130, 2007, pp. 316-319.
Kodaki, Tsutomu et al., "Biomass no Ethanol Henkan—Protein Kogakuteki Approach", ECO Industry, vol. 9, No. 5, pp. 38 to 44, (2004), (with partial English translation).
Watanabe, Seiya et al., "Complete Reversal of Coenzyme Specificity of Xylitol Dehydrogenase and Increase of Thermostability by the Introduction of Structural Zinc", The Journal of Biological Chemistry, vol. 280, No. 11, pp. 10340-10349, (2005).
Lima, Luanne Helena Augusto et al., "Xylitol dehydrogenase from *Candida tropicalis*: molecular cloning of the gene and structural analysis of the protein", Appl., Microbiol., Biotechnol., vol. 73, No. 3, pp. 631-639, (2006).
Matsushika, Akinori et al., "Bioethanol Production from Xylose by Recombinant *Saccharomyces cerevisiae* Expressing Xylose Reductase, NADP+-dependent Xylitol Dehydrogenase, and Xylulokinase", Journal of Bioscience and Bioengineering, vol. 105, No. 3, pp. 296-299, (Mar. 2008).
Japanese Office Action issued Sep. 4, 2012, in Japan Patent Application No. 2008-211274.

* cited by examiner

*Primary Examiner* — Tekchand Saidha
(74) *Attorney, Agent, or Firm* — Oblon, Spivak, McClelland, Maier & Neustadt, L.L.P.

(57) ABSTRACT

Genetic recombinant yeast expressing xylose reductase (XR), (wild-type or mutant) xylitol dehydrogenase (XDH), and xylulokinase (XK) and a method for highly efficiently producing ethanol from xylose using the yeast are provided. *Pichia stipitis*-derived XR and (wild-type or modified-type) XDH genes and *Saccharomyces cerevisiae*-derived XK gene were introduced via chromosomal integration. Thus, a genetic recombinant yeast having a high xylose fermentation rate, being capable of producing ethanol from xylose in high yields, and having high xylose fermentability in the presence of glucose, as well as a method using the recombinant yeast for highly efficiently producing ethanol from xylose or a saccharified solution from lignocellulose-based biomass are provided. Furthermore, a method for improving the xylose fermentability of the genetic recombinant yeast of the present invention via acclimatization treatment is also provided herein.

15 Claims, 10 Drawing Sheets

Fig. 3

| Strain | XR (U/mg) | XDH (U/mg) | | XK (U/mg) |
|---|---|---|---|---|
| | | NAD$^+$ | NADP$^+$ | |
| D-Control | 0.012 ± 0.005 | 0.002 ± 0.001 | 0.002 ± 0.001 | 0.019 ± 0.002 |
| D-WT | 0.135 ± 0.040 | 0.934 ± 0.091 | 0.006 ± 0.001 | 0.041 ± 0.005 |
| D-ARSdR | 0.179 ± 0.017 | 0.006 ± 0.001 | 0.119 ± 0.024 | 0.042 ± 0.004 |
| N-Control | 0.014 ± 0.001 | 0.004 ± 0.001 | 0.002 ± 0.001 | 0.019 ± 0.002 |
| N-WT | 0.139 ± 0.068 | 1.526 ± 0.060 | 0.007 ± 0.002 | 0.030 ± 0.004 |
| N-ARSdR | 0.133 ± 0.054 | 0.008 ± 0.003 | 0.225 ± 0.033 | 0.034 ± 0.007 |
| T-Control | 0.020 ± 0.002 | 0.003 ± 0.003 | 0.002 ± 0.001 | 0.016 ± 0.001 |
| T-WT | 0.244 ± 0.196 | 1.014 ± 0.875 | 0.005 ± 0.003 | 0.041 ± 0.004 |
| T-ARSdR | 0.388 ± 0.025 | 0.007 ± 0.004 | 0.026 ± 0.006 | 0.042 ± 0.005 |
| R-Control | 0.026 ± 0.005 | 0.005 ± 0.001 | 0.002 ± 0.001 | 0.020 ± 0.001 |
| R-WT | 0.791 ± 0.121 | 2.093 ± 0.314 | 0.007 ± 0.001 | 0.043 ± 0.008 |
| R-ARSdR | 1.240 ± 0.056 | 0.022 ± 0.001 | 0.129 ± 0.018 | 0.041 ± 0.006 |

*Values in Fig. 3 indicate average values of the results obtained by 3 independent experiments.

Fig. 8

| Strain | Host | Gene name | Saccharides (g/l) | *Ethanol yield (%) | #Time (hour) | References |
|---|---|---|---|---|---|---|
| S. cereviciae | 424A(LNH-ST) | XR, XDH, XK | Glc:Xyl=70:40 | 84 | 30 | 1) |
| S. cereviciae | TMB3255 | XR, XDH, XK Δzwf1 | Xyl 50 | 80 | 70 | 2) |
| S. cereviciae | TMB3120 | XR, XDH, XK ΔGRE3 | Xyl 10 | 90 | 72 | 3) |
| S. cereviciae | IR-2 (Kuriyama strain) | XR, Modified type XDH, XK | Xyl 45 | 72 | 33 | |
| S. cereviciae | IR-2 (Kuriyama strain) | XR, XDH, XK | Glc:Xyl=45:45 | 82 | 24 | |
| E. coli | KO11 | ADH, PDC | Xyl 90 | 89 | 48 | 4) |
| E. coli | KO11 | ADH, PDC | Ara:Gal:Glc:Xyl =23:11:27:39 | 90 | 72 | 5) |
| Z. mobilis | AX101 | XYLA, XYLB, TAL, TKTA | Ara:Glc:Xyl =20:40:40 | 84 | 96 | 6) |
| Z. palmae | ATCC51623 | XYLA, XYLB, TAL, TKTA | Xyl 40 | 91 | 120 | 7) |
| | | | Glc:Xyl=20:20 | 95 | 96 | 7) |

* Ethanol yield from total sugar consumption
Time required for almost complete consumption of xylose References
1) Sedlak and Ho (2004), Appl. Biochem. Biotechnol. Vol.113-116, pp. 403-416
2) Jeppsson et al. (2002), Appl. Environ. Microbiol. Vol.68, No.4, pp. 1604-1609
3) Traff-Bjerre et al. (2004), Yeast Vol.21, pp. 141-150
4) Yamano et al. (1998), J. Ind. Microbiol. Biotechnol. Vol.20, pp. 132-138
5) Asghari et al. (1996), J. Ind. Microbiol. Biotechnol. Vol.16, pp. 42-47
6) Mohagheghi et al. (2002), Appl. Biochem. Biotechnol. Vol.98, pp. 885-898
7) Yanase et al. (2007), Appl. Environ. Microbiol. Vol.72, No.8, pp. 2592-2599

SEQUENCE LISTING

```
<160> NUMBER OF SEQ ID NOS: 16

<210> SEQ ID NO 1
<211> LENGTH: 1092
<212> TYPE: DNA
<213> ORGANISM: Pichia stipitis
<220> FEATURE:
<221> NAME/KEY: CDS
<222> LOCATION: (1)..(1089)

<400> SEQUENCE: 1 atg act gct aac cct tcc ttg gtg ttg aac aag atc gac gac att tcg        48
Met Thr Ala Asn Pro Ser Leu Val Leu Asn Lys Ile Asp Asp Ile Ser
1               5                   10                  15 ttc gaa act tac gat gcc cca gaa atc tct gaa cct acc gat gtc ctc        96
Phe Glu Thr Tyr Asp Ala Pro Glu Ile Ser Glu Pro Thr Asp Val Leu
            20                  25                  30 gtc cag gtc aag aaa acc ggt atc tgt ggt tcc gac atc cac ttc tac       144
Val Gln Val Lys Lys Thr Gly Ile Cys Gly Ser Asp Ile His Phe Tyr
        35                  40                  45 gcc cat ggt aga atc ggt aac ttc gtt ttg acc aag cca atg gtc ttg       192
Ala His Gly Arg Ile Gly Asn Phe Val Leu Thr Lys Pro Met Val Leu
    50                  55                  60 ggt cac gaa tcc gcc ggt act gtt gtc cag gtt ggt aag ggt gtc acc       240
Gly His Glu Ser Ala Gly Thr Val Val Gln Val Gly Lys Gly Val Thr
65                  70                  75                  80 tct ctt aag gtt ggt gac aac gtc gct atc gaa cca ggt att cca tcc       288
Ser Leu Lys Val Gly Asp Asn Val Ala Ile Glu Pro Gly Ile Pro Ser
                85                  90                  95 aga ttc tcc gac gaa tac aag agc ggt cac tac aac ttg tgt cct cac       336
Arg Phe Ser Asp Glu Tyr Lys Ser Gly His Tyr Asn Leu Cys Pro His
```

```
atg gcc ttc gcc gct act cct aac tcc aag gaa ggc gaa cca aac cca      384
Met Ala Phe Ala Ala Thr Pro Asn Ser Lys Glu Gly Glu Pro Asn Pro
        115                 120                 125 cca ggt acc tta tgt aag tac ttc aag tcg cca gaa gac ttc ttg gtc      432
Pro Gly Thr Leu Cys Lys Tyr Phe Lys Ser Pro Glu Asp Phe Leu Val
130                 135                 140 aag ttg cca gac cac gtc agc ttg gaa ctc ggt gct ctt gtt gag cca      480
Lys Leu Pro Asp His Val Ser Leu Glu Leu Gly Ala Leu Val Glu Pro
145                 150                 155                 160 ttg tct gtt ggt gtc cac gcc tcc aag ttg ggt tcc gtt gct ttc ggc      528
Leu Ser Val Gly Val His Ala Ser Lys Leu Gly Ser Val Ala Phe Gly
                165                 170                 175 gac tac gtt gcc gtc ttt ggt gct ggt cct gtt ggt ctt ttg gct gct      576
Asp Tyr Val Ala Val Phe Gly Ala Gly Pro Val Gly Leu Leu Ala Ala
            180                 185                 190 gct gtc gcc aag acc ttc ggt gct aag ggt gtc atc gtc gtt gct aga      624
Ala Val Ala Lys Thr Phe Gly Ala Lys Gly Val Ile Val Val Ala Arg
        195                 200                 205 tcc gac aga aag ttg aag atg gcc aag gac att ggt gct gct act cac      672
Ser Asp Arg Lys Leu Lys Met Ala Lys Asp Ile Gly Ala Ala Thr His
210                 215                 220 acc ttc aac tcc aag acc ggt ggt tct gaa gaa ttg atc aag gct ttc      720
Thr Phe Asn Ser Lys Thr Gly Gly Ser Glu Glu Leu Ile Lys Ala Phe
225                 230                 235                 240 ggt ggt aac gtg cca aac gtc gtt ttg gaa tgt act ggt gct gaa cct      768
Gly Gly Asn Val Pro Asn Val Val Leu Glu Cys Thr Gly Ala Glu Pro
                245                 250                 255 tgt atc aag ttg ggt gtt gac gcc att gcc cca ggt ggt cgt ttc gtt      816
Cys Ile Lys Leu Gly Val Asp Ala Ile Ala Pro Gly Gly Arg Phe Val
            260                 265                 270 caa gtt ggt aac gct gct ggt cca gtc agc ttc cca atc acc gtt ttc      864
Gln Val Gly Asn Ala Ala Gly Pro Val Ser Phe Pro Ile Thr Val Phe
        275                 280                 285 gcc atg aag gaa ttg act ttg ttc ggt tct ttc aga tac gga ttc aac      912
Ala Met Lys Glu Leu Thr Leu Phe Gly Ser Phe Arg Tyr Gly Phe Asn
290                 295                 300 gac tac aag act gct gtt gga atc ttt gac act aac tac caa aac ggt      960
Asp Tyr Lys Thr Ala Val Gly Ile Phe Asp Thr Asn Tyr Gln Asn Gly
305                 310                 315                 320 aga gaa aat gct cca att gac ttt gaa caa ttg atc acc cac aga tac     1008
Arg Glu Asn Ala Pro Ile Asp Phe Glu Gln Leu Ile Thr His Arg Tyr
                325                 330                 335 aag ttc aag gac gct att gaa gcc tac gac ttg gtc aga gcc ggt aag     1056
Lys Phe Lys Asp Ala Ile Glu Ala Tyr Asp Leu Val Arg Ala Gly Lys
            340                 345                 350 ggt gct gtc aag tgt ctc att gac ggc cct gag taa                     1092
Gly Ala Val Lys Cys Leu Ile Asp Gly Pro Glu
        355                 360

<210> SEQ ID NO 2
<211> LENGTH: 1026
<212> TYPE: DNA
<213> ORGANISM: Pichia stipitis
<220> FEATURE:
<221> NAME/KEY: CDS
<222> LOCATION: (16)..(969)

<400> SEQUENCE: 2
tacaactata ctaca atg cct tct att aag ttg aac tct ggt tac gac atg     51
                Met Pro Ser Ile Lys Leu Asn Ser Gly Tyr Asp Met
                  1               5                  10
```

| | | |
|---|---|---|
| cca gcc gtc ggt ttc ggc tgt tgg aaa gtc gac gtc gac acc tgt tct<br>Pro Ala Val Gly Phe Gly Cys Trp Lys Val Asp Val Asp Thr Cys Ser<br>     15                  20               25 | | 99 |
| gaa cag atc tac cgt gct atc aag acc ggt tac aga ttg ttc gac ggt<br>Glu Gln Ile Tyr Arg Ala Ile Lys Thr Gly Tyr Arg Leu Phe Asp Gly<br> 30                  35                40 | | 147 |
| gcc gaa gat tac gcc aac gaa aag tta gtt ggt gcc ggt gtc aag aag<br>Ala Glu Asp Tyr Ala Asn Glu Lys Leu Val Gly Ala Gly Val Lys Lys<br>45               50                55              60 | | 195 |
| gcc att gac gaa ggt atc gtc aag cgt gaa gac ttg ttc ctt acc tcc<br>Ala Ile Asp Glu Gly Ile Val Lys Arg Glu Asp Leu Phe Leu Thr Ser<br>               65                70              75 | | 243 |
| aag ttg tgg aac aac tac cac cac cca gac aac gtc gaa aag gcc ttg<br>Lys Leu Trp Asn Asn Tyr His His Pro Asp Asn Val Glu Lys Ala Leu<br>        80                  85              90 | | 291 |
| aac aga acc ctt tct gac ttg caa gtt gac tac gtt gac ttg ttc ttg<br>Asn Arg Thr Leu Ser Asp Leu Gln Val Asp Tyr Val Asp Leu Phe Leu<br>           95                100            105 | | 339 |
| atc cac ttc cca gtc acc ttc aag ttc gtt cca tta gaa gaa aag tac<br>Ile His Phe Pro Val Thr Phe Lys Phe Val Pro Leu Glu Glu Lys Tyr<br>110                  115               120 | | 387 |
| cca cca gga ttc tac tgt ggt aag ggt gac aac ttc gac tac gaa gat<br>Pro Pro Gly Phe Tyr Cys Gly Lys Gly Asp Asn Phe Asp Tyr Glu Asp<br>125                  130               135             140 | | 435 |
| gtt cca att tta gag acc tgg aag gct ctt gaa aag ttg gtc aag gcc<br>Val Pro Ile Leu Glu Thr Trp Lys Ala Leu Glu Lys Leu Val Lys Ala<br>                  145               150             155 | | 483 |
| ggt aag atc aga tct atc ggt gtt tct aac ttc cca ggt gct ttg ctc<br>Gly Lys Ile Arg Ser Ile Gly Val Ser Asn Phe Pro Gly Ala Leu Leu<br>                    160              165              170 | | 531 |
| ttg gac ttg ttg aga ggt gct acc atc aag cca tct gtc ttg caa gtt<br>Leu Asp Leu Leu Arg Gly Ala Thr Ile Lys Pro Ser Val Leu Gln Val<br>          175                180              185 | | 579 |
| gaa cac cac cca tac ttg caa caa cca aga ttg atc gaa ttc gct caa<br>Glu His His Pro Tyr Leu Gln Gln Pro Arg Leu Ile Glu Phe Ala Gln<br>        190                195              200 | | 627 |
| tcc cgt ggt att gct gtc acc gct tac tct tcg ttc ggt cct caa tct<br>Ser Arg Gly Ile Ala Val Thr Ala Tyr Ser Ser Phe Gly Pro Gln Ser<br>205                  210               215             220 | | 675 |
| ttc gtt gaa ttg aac caa ggt aga gct ttg aac act tct cca ttg ttc<br>Phe Val Glu Leu Asn Gln Gly Arg Ala Leu Asn Thr Ser Pro Leu Phe<br>                    225              230              235 | | 723 |
| gag aac gaa act atc aag gct atc gct gct aag cac ggt aag tct cca<br>Glu Asn Glu Thr Ile Lys Ala Ile Ala Ala Lys His Gly Lys Ser Pro<br>                240              245              250 | | 771 |
| gct caa gtc ttg ttg aga tgg tct tcc caa aga ggc att gcc atc att<br>Ala Gln Val Leu Leu Arg Trp Ser Ser Gln Arg Gly Ile Ala Ile Ile<br>       255               260              265 | | 819 |
| cca aag tcc aac act gtc cca aga ttg ttg gaa aac aag gac gtc aac<br>Pro Lys Ser Asn Thr Val Pro Arg Leu Leu Glu Asn Lys Asp Val Asn<br>270                  275               280 | | 867 |
| agc ttc gac ttg gac gaa caa gat ttc gct gac att gcc aag ttg gac<br>Ser Phe Asp Leu Asp Glu Gln Asp Phe Ala Asp Ile Ala Lys Leu Asp<br>285                  290               295             300 | | 915 |
| atc aac ttg aga ttc aac gac cca tgg gac tgg gac aag att cct atc<br>Ile Asn Leu Arg Phe Asn Asp Pro Trp Asp Trp Asp Lys Ile Pro Ile<br>                    305              310              315 | | 963 |
| ttc gtc taagaaggtt gctttataga gaggaaataa aacctaatat acattgattg<br>Phe Val | | 1019 |

-continued

```
tacattt                                                          1026

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcataagctt atgccttcta ttaagttgaa ctctgg                              36

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
taaggatcct tagacgaagg ataggaatct tgtcc                               35

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cccggatccg ggaaataaat tgaattgaat tgaaatcg                            38

<210> SEQ ID NO 6
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gacactagtc tcgagcagct ttaacgaacg cagaattttc g                        41

<210> SEQ ID NO 7
<211> LENGTH: 1092
<212> TYPE: DNA
<213> ORGANISM: Pichia stipitis
<220> FEATURE:
<221> NAME/KEY: CDS
<222> LOCATION: (1)..(1089)

<400> SEQUENCE: 7 atg act gct aac cct tcc ttg gtg ttg aac aag atc gac gac att tcg     48
Met Thr Ala Asn Pro Ser Leu Val Leu Asn Lys Ile Asp Asp Ile Ser
1               5                   10                  15 ttc gaa act tac gat gcc cca gaa atc tct gaa cct acc gat gtc ctc     96
Phe Glu Thr Tyr Asp Ala Pro Glu Ile Ser Glu Pro Thr Asp Val Leu
            20                  25                  30 gtc cag gtc aag aaa acc ggt atc tgt ggt tcc gac atc cac ttc tac    144
Val Gln Val Lys Lys Thr Gly Ile Cys Gly Ser Asp Ile His Phe Tyr
        35                  40                  45 gcc cat ggt aga atc ggt aac ttc gtt ttg acc aag cca atg gtc ttg    192
Ala His Gly Arg Ile Gly Asn Phe Val Leu Thr Lys Pro Met Val Leu
    50                  55                  60
```

```
ggt cac gaa tcc gcc ggt act gtt gtc cag gtt ggt aag ggt gtc acc      240
Gly His Glu Ser Ala Gly Thr Val Val Gln Val Gly Lys Gly Val Thr
 65              70                  75                  80 tct ctt aag gtt ggt gac aac gtc gct atc gaa cca ggt att cca tcc      288
Ser Leu Lys Val Gly Asp Asn Val Ala Ile Glu Pro Gly Ile Pro Ser
                 85                  90                  95 aga ttc tcc gac gaa tac aag agc ggt cac tac aac ttg tgt cct cac      336
Arg Phe Ser Asp Glu Tyr Lys Ser Gly His Tyr Asn Leu Cys Pro His
            100                 105                 110 atg gcc ttc gcc gct act cct aac tcc aag gaa ggc gaa cca aac cca      384
Met Ala Phe Ala Ala Thr Pro Asn Ser Lys Glu Gly Glu Pro Asn Pro
        115                 120                 125 cca ggt acc tta tgt aag tac ttc aag tcg cca gaa gac ttc ttg gtc      432
Pro Gly Thr Leu Cys Lys Tyr Phe Lys Ser Pro Glu Asp Phe Leu Val
    130                 135                 140 aag ttg cca gac cac gtc agc ttg gaa ctc ggt gct ctt gtt gag cca      480
Lys Leu Pro Asp His Val Ser Leu Glu Leu Gly Ala Leu Val Glu Pro
145                 150                 155                 160 ttg tct gtt ggt gtc cac gcc tcc aag ttg ggt tcc gtt gct ttc ggc      528
Leu Ser Val Gly Val His Ala Ser Lys Leu Gly Ser Val Ala Phe Gly
                165                 170                 175 gac tac gtt gcc gtc ttt ggt gct ggt cct gtt ggt ctt ttg gct gct      576
Asp Tyr Val Ala Val Phe Gly Ala Gly Pro Val Gly Leu Leu Ala Ala
            180                 185                 190 gct gtc gcc aag acc ttc ggt gct aag ggt gtc atc gtc gtt gac att      624
Ala Val Ala Lys Thr Phe Gly Ala Lys Gly Val Ile Val Val Asp Ile
        195                 200                 205 ttc gac aac aag ttg aag atg gcc aag gac att ggt gct gct act cac      672
Phe Asp Asn Lys Leu Lys Met Ala Lys Asp Ile Gly Ala Ala Thr His
    210                 215                 220 acc ttc aac tcc aag acc ggt ggt tct gaa gaa ttg atc aag gct ttc      720
Thr Phe Asn Ser Lys Thr Gly Gly Ser Glu Glu Leu Ile Lys Ala Phe
225                 230                 235                 240 ggt ggt aac gtg cca aac gtc gtt ttg gaa tgt act ggt gct gaa cct      768
Gly Gly Asn Val Pro Asn Val Val Leu Glu Cys Thr Gly Ala Glu Pro
                245                 250                 255 tgt atc aag ttg ggt gtt gac gcc att gcc cca ggt ggt cgt ttc gtt      816
Cys Ile Lys Leu Gly Val Asp Ala Ile Ala Pro Gly Gly Arg Phe Val
            260                 265                 270 caa gtt ggt aac gct gct ggt cca gtc agc ttc cca atc acc gtt ttc      864
Gln Val Gly Asn Ala Ala Gly Pro Val Ser Phe Pro Ile Thr Val Phe
        275                 280                 285 gcc atg aag gaa ttg act ttg ttc ggt tct ttc aga tac gga ttc aac      912
Ala Met Lys Glu Leu Thr Leu Phe Gly Ser Phe Arg Tyr Gly Phe Asn
    290                 295                 300 gac tac aag act gct gtt gga atc ttt gac act aac tac caa aac ggt      960
Asp Tyr Lys Thr Ala Val Gly Ile Phe Asp Thr Asn Tyr Gln Asn Gly
305                 310                 315                 320 aga gaa aat gct cca att gac ttt gaa caa ttg atc acc cac aga tac     1008
Arg Glu Asn Ala Pro Ile Asp Phe Glu Gln Leu Ile Thr His Arg Tyr
                325                 330                 335 aag ttc aag gac gct att gaa gcc tac gac ttg gtc aga gcc ggt aag     1056
Lys Phe Lys Asp Ala Ile Glu Ala Tyr Asp Leu Val Arg Ala Gly Lys
            340                 345                 350 ggt gct gtc aag tgt ctc att gac ggc cct gag taa                     1092
Gly Ala Val Lys Cys Leu Ile Asp Gly Pro Glu
        355                 360

<210> SEQ ID NO 8
<211> LENGTH: 33
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
catgaattca tgactgctaa cccttccttg gtg                                    33

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
taaggatcct tactcagggc cgtcaatgag ac                                     32

<210> SEQ ID NO 10
<211> LENGTH: 1803
<212> TYPE: DNA
<213> ORGANISM: Saccharomyces cerevisiae
<220> FEATURE:
<221> NAME/KEY: CDS
<222> LOCATION: (1)..(1800)

<400> SEQUENCE: 10
```

| | | | | | | | | | | | | | | | | |
|---|---|---|---|---|---|---|---|---|---|---|---|---|---|---|---|---|
| atg | ttg | tgt | tca | gta | att | cag | aga | cag | aca | aga | gag | gtt | tcc | aac | aca | 48 |
| Met | Leu | Cys | Ser | Val | Ile | Gln | Arg | Gln | Thr | Arg | Glu | Val | Ser | Asn | Thr | |
| 1 | | | | 5 | | | | | 10 | | | | | 15 | | |
| atg | tct | tta | gac | tca | tac | tat | ctt | ggg | ttt | gat | ctt | tcg | acc | caa | caa | 96 |
| Met | Ser | Leu | Asp | Ser | Tyr | Tyr | Leu | Gly | Phe | Asp | Leu | Ser | Thr | Gln | Gln | |
| | | 20 | | | | | 25 | | | | | 30 | | | | |
| ctg | aaa | tgt | ctc | gcc | att | aac | cag | gac | cta | aaa | att | gtc | cat | tca | gaa | 144 |
| Leu | Lys | Cys | Leu | Ala | Ile | Asn | Gln | Asp | Leu | Lys | Ile | Val | His | Ser | Glu | |
| | | | 35 | | | | | 40 | | | | | 45 | | | |
| aca | gtg | gaa | ttt | gaa | aag | gat | ctt | ccg | cat | tat | cac | aca | aag | aag | ggt | 192 |
| Thr | Val | Glu | Phe | Glu | Lys | Asp | Leu | Pro | His | Tyr | His | Thr | Lys | Lys | Gly | |
| | 50 | | | | | 55 | | | | | 60 | | | | | |
| gtc | tat | ata | cac | ggc | gac | act | atc | gaa | tgt | ccc | gta | gcc | atg | tgg | tta | 240 |
| Val | Tyr | Ile | His | Gly | Asp | Thr | Ile | Glu | Cys | Pro | Val | Ala | Met | Trp | Leu | |
| 65 | | | | | 70 | | | | | 75 | | | | | 80 | |
| gag | gct | cta | gat | ctg | gtt | ctc | tcg | aaa | tat | cgc | gag | gct | aaa | ttt | cca | 288 |
| Glu | Ala | Leu | Asp | Leu | Val | Leu | Ser | Lys | Tyr | Arg | Glu | Ala | Lys | Phe | Pro | |
| | | | | 85 | | | | | 90 | | | | | 95 | | |
| ttg | aac | aaa | gtt | atg | gcc | gtc | tca | ggg | tcc | tgc | cag | cag | cac | ggg | tct | 336 |
| Leu | Asn | Lys | Val | Met | Ala | Val | Ser | Gly | Ser | Cys | Gln | Gln | His | Gly | Ser | |
| | | | 100 | | | | | 105 | | | | | 110 | | | |
| gtc | tac | tgg | tcc | tcc | caa | gcc | gaa | tct | ctg | tta | gag | caa | ttg | aat | aag | 384 |
| Val | Tyr | Trp | Ser | Ser | Gln | Ala | Glu | Ser | Leu | Leu | Glu | Gln | Leu | Asn | Lys | |
| | | 115 | | | | | 120 | | | | | 125 | | | | |
| aaa | ccg | gaa | aaa | gat | tta | ttg | cac | tac | gtg | agc | tct | gta | gca | ttt | gca | 432 |
| Lys | Pro | Glu | Lys | Asp | Leu | Leu | His | Tyr | Val | Ser | Ser | Val | Ala | Phe | Ala | |
| | 130 | | | | | 135 | | | | | 140 | | | | | |
| agg | caa | acc | gcc | ccc | aat | tgg | caa | gac | cac | agt | act | gca | aag | caa | tgt | 480 |
| Arg | Gln | Thr | Ala | Pro | Asn | Trp | Gln | Asp | His | Ser | Thr | Ala | Lys | Gln | Cys | |
| 145 | | | | | 150 | | | | | 155 | | | | | 160 | |
| caa | gag | ttt | gaa | gag | tgc | ata | ggt | ggg | cct | gaa | aaa | atg | gct | caa | tta | 528 |
| Gln | Glu | Phe | Glu | Glu | Cys | Ile | Gly | Gly | Pro | Glu | Lys | Met | Ala | Gln | Leu | |
| | | | | 165 | | | | | 170 | | | | | 175 | | |
| aca | ggg | tcc | aga | gcc | cat | ttt | aga | ttt | act | ggt | cct | caa | att | ctg | aaa | 576 |
| Thr | Gly | Ser | Arg | Ala | His | Phe | Arg | Phe | Thr | Gly | Pro | Gln | Ile | Leu | Lys | |

```
                180                 185                 190
att gca caa tta gaa cca gaa gct tac gaa aaa aca aag acc att tct    624
Ile Ala Gln Leu Glu Pro Glu Ala Tyr Glu Lys Thr Lys Thr Ile Ser
        195                 200                 205 tta gtg tct aat ttt ttg act tct atc tta gtg ggc cat ctt gtt gaa    672
Leu Val Ser Asn Phe Leu Thr Ser Ile Leu Val Gly His Leu Val Glu
210                 215                 220 tta gag gag gca gat gcc tgt ggt atg aac ctt tat gat ata cgt gaa    720
Leu Glu Glu Ala Asp Ala Cys Gly Met Asn Leu Tyr Asp Ile Arg Glu
225                 230                 235                 240 aga aaa ttc agt gat gag cta cta cat cta att gat agt tct tct aag    768
Arg Lys Phe Ser Asp Glu Leu Leu His Leu Ile Asp Ser Ser Ser Lys
            245                 250                 255 gat aaa act atc aga caa aaa tta atg aga gca ccc atg aaa aat ttg    816
Asp Lys Thr Ile Arg Gln Lys Leu Met Arg Ala Pro Met Lys Asn Leu
        260                 265                 270 ata gcg ggt acc atc tgt aaa tat ttt att gag aag tac ggt ttc aat    864
Ile Ala Gly Thr Ile Cys Lys Tyr Phe Ile Glu Lys Tyr Gly Phe Asn
    275                 280                 285 aca aac tgc aag gtc tct ccc atg act ggg gat aat tta gcc act ata    912
Thr Asn Cys Lys Val Ser Pro Met Thr Gly Asp Asn Leu Ala Thr Ile
290                 295                 300 tgt tct tta ccc ctg cgg aag aat gac gtt ctc gtt tcc cta gga aca    960
Cys Ser Leu Pro Leu Arg Lys Asn Asp Val Leu Val Ser Leu Gly Thr
305                 310                 315                 320 agt act aca gtt ctt ctg gtc acc gat aag tat cac ccc tct ccg aac   1008
Ser Thr Thr Val Leu Leu Val Thr Asp Lys Tyr His Pro Ser Pro Asn
            325                 330                 335 tat cat ctt ttc att cat cca act ctg cca aac cat tat atg ggt atg   1056
Tyr His Leu Phe Ile His Pro Thr Leu Pro Asn His Tyr Met Gly Met
        340                 345                 350 att tgt tat tgt aat ggt tct ttg gca agg gag agg ata aga gac gag   1104
Ile Cys Tyr Cys Asn Gly Ser Leu Ala Arg Glu Arg Ile Arg Asp Glu
    355                 360                 365 tta aac aaa gaa cgg gaa aat aat tat gag aag act aac gat tgg act   1152
Leu Asn Lys Glu Arg Glu Asn Asn Tyr Glu Lys Thr Asn Asp Trp Thr
370                 375                 380 ctt ttt aat caa gct gtg cta gat gac tca gaa agt agt gaa aat gaa   1200
Leu Phe Asn Gln Ala Val Leu Asp Asp Ser Glu Ser Ser Glu Asn Glu
385                 390                 395                 400 tta ggt gta tat ttt cct ctg ggg gag atc gtt cct agc gta aaa gcc   1248
Leu Gly Val Tyr Phe Pro Leu Gly Glu Ile Val Pro Ser Val Lys Ala
            405                 410                 415 ata aac aaa agg gtt atc ttc aat cca aaa acg ggt atg att gaa aga   1296
Ile Asn Lys Arg Val Ile Phe Asn Pro Lys Thr Gly Met Ile Glu Arg
        420                 425                 430 gag gtg gcc aag ttc aaa gac aag agg cac gat gcc aaa aat att gta   1344
Glu Val Ala Lys Phe Lys Asp Lys Arg His Asp Ala Lys Asn Ile Val
    435                 440                 445 gaa tca cag gct tta agt tgc agg gta aga ata tct ccc ctg ctt tcg   1392
Glu Ser Gln Ala Leu Ser Cys Arg Val Arg Ile Ser Pro Leu Leu Ser
450                 455                 460 gat tca aac gca agc tca caa cag aga ctg aac gaa gat aca atc gtg   1440
Asp Ser Asn Ala Ser Ser Gln Gln Arg Leu Asn Glu Asp Thr Ile Val
465                 470                 475                 480 aag ttt gat tac gat gaa tct ccg ctg cgg gac tac cta aat aaa agg   1488
Lys Phe Asp Tyr Asp Glu Ser Pro Leu Arg Asp Tyr Leu Asn Lys Arg
            485                 490                 495 cca gaa agg act ttt ttt gta ggt ggg gct tct aaa aac gat gct att   1536
Pro Glu Arg Thr Phe Phe Val Gly Gly Ala Ser Lys Asn Asp Ala Ile
```

```
                     500                 505                 510
gtg aag aag ttt gct caa gtc att ggt gct aca aag ggt aat ttt agg        1584
Val Lys Lys Phe Ala Gln Val Ile Gly Ala Thr Lys Gly Asn Phe Arg
        515                 520                 525 cta gaa aca cca aac tca tgt gcc ctt ggt ggt tgt tat aag gcc atg        1632
Leu Glu Thr Pro Asn Ser Cys Ala Leu Gly Gly Cys Tyr Lys Ala Met
    530                 535                 540 tgg tca ttg tta tat gac tct aat aaa att gca gtt cct ttt gat aaa        1680
Trp Ser Leu Leu Tyr Asp Ser Asn Lys Ile Ala Val Pro Phe Asp Lys
545                 550                 555                 560 ttt ctg aat gac aat ttt cca tgg cat gta atg gaa agc ata tcc gat        1728
Phe Leu Asn Asp Asn Phe Pro Trp His Val Met Glu Ser Ile Ser Asp
                565                 570                 575 gtg gat aat gaa aat tgg gat cgc tat aat tcc aag att gtc ccc tta        1776
Val Asp Asn Glu Asn Trp Asp Arg Tyr Asn Ser Lys Ile Val Pro Leu
            580                 585                 590 agc gaa ctg gaa aag act ctc atc taa                                    1803
Ser Glu Leu Glu Lys Thr Leu Ile
        595                 600

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
catgaattca tgttgtgttc agtaattcag agacagac                              38

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
taaggatcct tagatgagag tcttttccag ttcgc                                 35

<210> SEQ ID NO 13
<211> LENGTH: 363
<212> TYPE: PRT
<213> ORGANISM: Pichia stipitis

<400> SEQUENCE: 13

Met Thr Ala Asn Pro Ser Leu Val Leu Asn Lys Ile Asp Asp Ile Ser
1               5                   10                  15

Phe Glu Thr Tyr Asp Ala Pro Glu Ile Ser Glu Pro Thr Asp Val Leu
            20                  25                  30

Val Gln Val Lys Lys Thr Gly Ile Cys Gly Ser Asp Ile His Phe Tyr
        35                  40                  45

Ala His Gly Arg Ile Gly Asn Phe Val Leu Thr Lys Pro Met Val Leu
    50                  55                  60

Gly His Glu Ser Ala Gly Thr Val Val Gln Val Gly Lys Gly Val Thr
65                  70                  75                  80

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
            100                 105                 110
```

```
Met Ala Phe Ala Ala Thr Pro Asn Ser Lys Glu Gly Glu Pro Asn Pro
            115                 120                 125

Pro Gly Thr Leu Cys Lys Tyr Phe Lys Ser Pro Glu Asp Phe Leu Val
    130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175

Asp Tyr Val Ala Val Phe Gly Ala Gly Pro Val Gly Leu Leu Ala Ala
            180                 185                 190

Ala Val Ala Lys Thr Phe Gly Ala Lys Gly Val Ile Val Val Ala Arg
        195                 200                 205

Ser Asp Arg Lys Leu Lys Met Ala Lys Asp Ile Gly Ala Ala Thr His
    210                 215                 220

Thr Phe Asn Ser Lys Thr Gly Gly Ser Glu Glu Leu Ile Lys Ala Phe
225                 230                 235                 240

Gly Gly Asn Val Pro Asn Val Val Leu Glu Cys Thr Gly Ala Glu Pro
                245                 250                 255

Cys Ile Lys Leu Gly Val Asp Ala Ile Ala Pro Gly Gly Arg Phe Val
            260                 265                 270

Gln Val Gly Asn Ala Ala Gly Pro Val Ser Phe Pro Ile Thr Val Phe
        275                 280                 285

Ala Met Lys Glu Leu Thr Leu Phe Gly Ser Phe Arg Tyr Gly Phe Asn
    290                 295                 300

Asp Tyr Lys Thr Ala Val Gly Ile Phe Asp Thr Asn Tyr Gln Asn Gly
305                 310                 315                 320

Arg Glu Asn Ala Pro Ile Asp Phe Glu Gln Leu Ile Thr His Arg Tyr
                325                 330                 335

Lys Phe Lys Asp Ala Ile Glu Ala Tyr Asp Leu Val Arg Ala Gly Lys
            340                 345                 350

Gly Ala Val Lys Cys Leu Ile Asp Gly Pro Glu
        355                 360

<210> SEQ ID NO 14
<211> LENGTH: 318
<212> TYPE: PRT
<213> ORGANISM: Pichia stipitis

<400> SEQUENCE: 14

Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125
```

Tyr Cys Gly Lys Gly Asp Asn Phe Asp Tyr Glu Asp Val Pro Ile Leu
            130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Arg Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315

<210> SEQ ID NO 15
<211> LENGTH: 363
<212> TYPE: PRT
<213> ORGANISM: Pichia stipitis

<400> SEQUENCE: 15

Met Thr Ala Asn Pro Ser Leu Val Leu Asn Lys Ile Asp Asp Ile Ser
1               5                   10                  15

Phe Glu Thr Tyr Asp Ala Pro Glu Ile Ser Glu Pro Thr Asp Val Leu
            20                  25                  30

Val Gln Val Lys Lys Thr Gly Ile Cys Gly Ser Asp Ile His Phe Tyr
        35                  40                  45

Ala His Gly Arg Ile Gly Asn Phe Val Leu Thr Lys Pro Met Val Leu
    50                  55                  60

Gly His Glu Ser Ala Gly Thr Val Val Gln Val Gly Lys Gly Val Thr
65                  70                  75                  80

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
            100                 105                 110

Met Ala Phe Ala Ala Thr Pro Asn Ser Lys Glu Gly Glu Pro Asn Pro
        115                 120                 125

Pro Gly Thr Leu Cys Lys Tyr Phe Lys Ser Pro Glu Asp Phe Leu Val
    130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175

Asp Tyr Val Ala Val Phe Gly Ala Gly Pro Val Gly Leu Leu Ala Ala
            180                 185                 190

-continued

```
Ala Val Ala Lys Thr Phe Gly Ala Lys Gly Val Ile Val Val Asp Ile
        195                 200                 205

Phe Asp Asn Lys Leu Lys Met Ala Lys Asp Ile Gly Ala Ala Thr His
210                 215                 220

Thr Phe Asn Ser Lys Thr Gly Gly Ser Glu Glu Leu Ile Lys Ala Phe
225                 230                 235                 240

Gly Gly Asn Val Pro Asn Val Val Leu Glu Cys Thr Gly Ala Glu Pro
                245                 250                 255

Cys Ile Lys Leu Gly Val Asp Ala Ile Ala Pro Gly Gly Arg Phe Val
            260                 265                 270

Gln Val Gly Asn Ala Ala Gly Pro Val Ser Phe Pro Ile Thr Val Phe
        275                 280                 285

Ala Met Lys Glu Leu Thr Leu Phe Gly Ser Phe Arg Tyr Gly Phe Asn
    290                 295                 300

Asp Tyr Lys Thr Ala Val Gly Ile Phe Asp Thr Asn Tyr Gln Asn Gly
305                 310                 315                 320

Arg Glu Asn Ala Pro Ile Asp Phe Glu Gln Leu Ile Thr His Arg Tyr
                325                 330                 335

Lys Phe Lys Asp Ala Ile Glu Ala Tyr Asp Leu Val Arg Ala Gly Lys
            340                 345                 350

Gly Ala Val Lys Cys Leu Ile Asp Gly Pro Glu
        355                 360

<210> SEQ ID NO 16
<211> LENGTH: 600
<212> TYPE: PRT
<213> ORGANISM: Saccharomyces cerevisiae

<400> SEQUENCE: 16

Met Leu Cys Ser Val Ile Gln Arg Gln Thr Arg Glu Val Ser Asn Thr
1               5                   10                  15

Met Ser Leu Asp Ser Tyr Tyr Leu Gly Phe Asp Leu Ser Thr Gln Gln
            20                  25                  30

Leu Lys Cys Leu Ala Ile Asn Gln Asp Leu Lys Ile Val His Ser Glu
        35                  40                  45

Thr Val Glu Phe Glu Lys Asp Leu Pro His Tyr His Thr Lys Lys Gly
    50                  55                  60

Val Tyr Ile His Gly Asp Thr Ile Glu Cys Pro Val Ala Met Trp Leu
65                  70                  75                  80

Glu Ala Leu Asp Leu Val Leu Ser Lys Tyr Arg Glu Ala Lys Phe Pro
                85                  90                  95

Leu Asn Lys Val Met Ala Val Ser Gly Ser Cys Gln Gln His Gly Ser
            100                 105                 110

Val Tyr Trp Ser Ser Gln Ala Glu Ser Leu Leu Glu Gln Leu Asn Lys
        115                 120                 125

Lys Pro Glu Lys Asp Leu Leu His Tyr Val Ser Ser Val Ala Phe Ala
    130                 135                 140

Arg Gln Thr Ala Pro Asn Trp Gln Asp His Ser Thr Ala Lys Gln Cys
145                 150                 155                 160

Gln Glu Phe Glu Glu Cys Ile Gly Gly Pro Glu Lys Met Ala Gln Leu
                165                 170                 175

Thr Gly Ser Arg Ala His Phe Arg Phe Thr Gly Pro Gln Ile Leu Lys
            180                 185                 190

Ile Ala Gln Leu Glu Pro Glu Ala Tyr Glu Lys Thr Lys Thr Ile Ser
        195                 200                 205
```

-continued

```
Leu Val Ser Asn Phe Leu Thr Ser Ile Leu Val Gly His Leu Val Glu
    210                 215                 220
Leu Glu Glu Ala Asp Ala Cys Gly Met Asn Leu Tyr Asp Ile Arg Glu
225                 230                 235                 240
Arg Lys Phe Ser Asp Glu Leu Leu His Leu Ile Asp Ser Ser Lys
                245                 250                 255
Asp Lys Thr Ile Arg Gln Lys Leu Met Arg Ala Pro Met Lys Asn Leu
            260                 265                 270
Ile Ala Gly Thr Ile Cys Lys Tyr Phe Ile Glu Lys Tyr Gly Phe Asn
            275                 280                 285
Thr Asn Cys Lys Val Ser Pro Met Thr Gly Asp Asn Leu Ala Thr Ile
    290                 295                 300
Cys Ser Leu Pro Leu Arg Lys Asn Asp Val Leu Val Ser Leu Gly Thr
305                 310                 315                 320
Ser Thr Thr Val Leu Leu Val Thr Asp Lys Tyr His Pro Ser Pro Asn
                325                 330                 335
Tyr His Leu Phe Ile His Pro Thr Leu Pro Asn His Tyr Met Gly Met
            340                 345                 350
Ile Cys Tyr Cys Asn Gly Ser Leu Ala Arg Glu Arg Ile Arg Asp Glu
            355                 360                 365
Leu Asn Lys Glu Arg Glu Asn Asn Tyr Glu Lys Thr Asn Asp Trp Thr
    370                 375                 380
Leu Phe Asn Gln Ala Val Leu Asp Asp Ser Glu Ser Ser Glu Asn Glu
385                 390                 395                 400
Leu Gly Val Tyr Phe Pro Leu Gly Glu Ile Val Pro Ser Val Lys Ala
                405                 410                 415
Ile Asn Lys Arg Val Ile Phe Asn Pro Lys Thr Gly Met Ile Glu Arg
            420                 425                 430
Glu Val Ala Lys Phe Lys Asp Lys Arg His Asp Ala Lys Asn Ile Val
            435                 440                 445
Glu Ser Gln Ala Leu Ser Cys Arg Val Arg Ile Ser Pro Leu Leu Ser
    450                 455                 460
Asp Ser Asn Ala Ser Ser Gln Gln Arg Leu Asn Glu Asp Thr Ile Val
465                 470                 475                 480
Lys Phe Asp Tyr Asp Glu Ser Pro Leu Arg Asp Tyr Leu Asn Lys Arg
                485                 490                 495
Pro Glu Arg Thr Phe Phe Val Gly Gly Ala Ser Lys Asn Asp Ala Ile
            500                 505                 510
Val Lys Lys Phe Ala Gln Val Ile Gly Ala Thr Lys Gly Asn Phe Arg
            515                 520                 525
Leu Glu Thr Pro Asn Ser Cys Ala Leu Gly Gly Cys Tyr Lys Ala Met
    530                 535                 540
Trp Ser Leu Leu Tyr Asp Ser Asn Lys Ile Ala Val Pro Phe Asp Lys
545                 550                 555                 560
Phe Leu Asn Asp Asn Phe Pro Trp His Val Met Glu Ser Ile Ser Asp
                565                 570                 575
Val Asp Asn Glu Asn Trp Asp Arg Tyr Asn Ser Lys Ile Val Pro Leu
            580                 585                 590
Ser Glu Leu Glu Lys Thr Leu Ile
            595                 600
```

HEXOSE-PENTOSE COFERMENTING YEAST HAVING EXCELLENT XYLOSE FERMENTABILITY AND METHOD FOR HIGHLY EFFICIENTLY PRODUCING ETHANOL USING THE SAME

CROSS-REFERENCE TO RELATED APPLICATIONS

The present application is a 35 U.S.C. §371 National Stage patent application of International patent application PCT/JP2009/050929, filed on Jan. 22, 2009, which claims priority to Japanese patent applications JP 2008-211274, filed on Aug. 20, 2008, and JP 2008-014080, filed on Jan. 24, 2008.

TECHNICAL FIELD

The present invention relates to a genetic recombinant yeast capable of fermenting xylose even in the presence of glucose, in addition to exhibiting a high xylose fermentation rate and producing a high yield of ethanol from xylose. The present invention also relates to a method for highly efficiently producing ethanol from xylose or a saccharified solution containing xylose using the same.

BACKGROUND ART

In recent years, demand for bioethanol is rapidly increasing in other countries because of countermeasures against global warming or the need of an alternate for fossil resource. A yeast (Saccharomyces cerevisiae) having high fermentation efficiency is the leader in bioethanol production. In the '70s, studies were actively conducted concerning Zymomonas mobilis, which is an ethanol-producing bacterium. From the late 80s, ethanol production by genetic recombinant Escherichia coli was reported. S. cerevisiae or Z. mobilis, known as a bacterium producing ethanol at a high concentration is unable to use xylose or arabinose, which is a pentose. In contrast, E. coli can use all saccharides listed herein, but its productivity per individual microorganism is lower than that of S. cerevisiae or Z. mobilis. For establishment of effective ethanol-producing technology from wood-based biomass, development of a microorganism that effectively produces ethanol from pentose is an important research project. In particular, it is desired to develop a microorganism highly efficiently converting xylose, which is richly contained in a saccharified solution of wood-based biomass, to ethanol. Regarding provision of xylose fermentability to yeast, the group of Dr. Ho of Purdue University and a group from Lund University have succeeded (see FIG. 8). Meanwhile, Dr. Ingram of the University of Florida has succeeded in such provision of xylose fermentability by introducing 2 types of ethanol synthase gene from Z. mobilis. A group of the National Renewable Energy Laboratory (NREL) has succeeded in provision by introducing 4 types of xylose metabolic enzyme gene from Escherichia coli (see FIG. 8). Furthermore, xylose fermentability has been successfully provided to novel microorganisms such as Zymobacter (Zymobacter palmae) by Dr. Yanase of Tottori University and to coryneform-group bacteria by the Dr. Yukawa of the Research Institute of Innovative Technology for the Earth (RITE). However, there still remain many challenges for practical application (such as improvement in xylose fermentability (ethanol yield and fermentation rate)) of all of these genetic recombinant microorganisms.

Pichia stipitis or the like is known as a yeast capable of fermenting xylose, but its ethanol resistance is low and its xylose metabolic system is often suppressed in the presence of saccharides such as glucose. For the production of ethanol from xylose, breeding is underway by introducing genes encoding P. stipitis-derived xylose reductase (hereinafter, referred to as "XR") and xylitol dehydrogenase into S. cerevisiae, so that the yeast acquires the ability to metabolize xylose (Non-patent documents 1, 2, and 3) (see FIG. 1).

However, such a genetic recombinant yeast is unsatisfactory, since the efficiency of anaerobic fermentation of ethanol from xylose is sill low. Moreover, the yeast is also problematic in that in the course of fermentation, an intermediate metabolite, xylitol, is accumulated, so as to lower carbon conversion efficiency. These defects are major hurdles for increasing the efficiency of continuous and/or serial fermentation processes in effective production of ethanol from wood-based biomass.

One major cause of such low ethanol conversion efficiency is an unbalanced intracellular redox status due to a difference in coenzyme dependency between xylose-metabolizing enzymes (XR and XDH) (Non-patent documents 4 and 5). Specifically, XR converts xylose to xylitol using mainly NADPH as a coenzyme for conversion to $NADP^+$, while XDH converts xylitol to xylulose using mainly $NAD^+$ as a coenzyme for conversion to NADH upon conversion (see FIG. 1). As described above, because of the resulting lack of balance of requirements for coenzymes between the two enzymes, the quantitative balance in coenzyme supply is disturbed. As a result, it is inferred that xylitol to xylulose conversion proceeds inefficiently, and ultimately the efficiency of xylose to ethanol conversion is lowered.

Furthermore, the fact that the activity of xylulokinase (hereinafter, referred to as XK), which is originally retained by S. cerevisiae is weak is also suggested as a cause of such low ethanol conversion efficiency (Non-patent documents 6 and 7). A method has been reported as a measure for improving the matter, which involves causing overexpression of S. cerevisiae-derived XK in addition to XR and XDH and then improving xylose to ethanol production efficiency using the recombinant yeast (see Patent document 1). It has also been reported that in such a case, expression of XR, XDH, and XK within yeast at appropriate levels is extremely important. For example, the proportions of the optimum expression levels of XR and XDH necessary to increase xylose to ethanol production efficiency are almost completely understood (Non-patent documents 8, 9, and 10). However, the optimum level of XK is controversial. Specifically, Dr. Ho of Purdue University has reported that high XK activity is important. Actually, high yields of ethanol have been obtained from xylose using the Saccharomyces yeast 424A (LNH-ST) strain, which has the ability to metabolize xylose provided via gene recombination (Non-patent document 8). In the meantime, Lund university and other groups have reported that genetic recombinant yeast strains were prepared from experimental strains (in which genes encoding XR, XDH, and XK, respectively, had been separately integrated onto different chromosomes using auxotrophic expression cassettes) and the genes are preferably appropriately expressed constitutively since excessive XK activity inhibits the growth of yeast (Non-patent documents 7 and 11).

Also, a method has been reported that involves preparing XDH (modified-type XDH) by converting its specificity for a coenzyme from $NAD^+$ requirement to $NADP^+$ requirement, preparing a genetic recombinant yeast co-expressing the modified-type XDH together with XR, and then producing ethanol from xylose using the genetic recombinant yeast (see Patent document 2 and FIG. 1).

In recent years, the use of ethanol or the like obtained by fermentation of a biomass resource as liquid fuel or a chemical raw material has been examined and is attracting attention. The technological development for practical use thereof is being accelerated. Therefore, economy for practical use of a biomass resource requires a yeast strain more highly capable of producing ethanol than the above yeast.

[Patent document 1] JP Patent Publication (Kohyo) No. 2000-509988 A

[Patent document 2] JP Patent Publication (Kokai) No. 2006-6213 A

[Patent document 3] JP Patent Publication (Kokai) No. 62-65679 A (1987)

[Non-patent document 1] Chu B C et al., Biotechnology Advances, Vol. 25, pp. 425-441 (2007)

[Non-patent document 2] Jeffries T W, Current opinion in Biotechnology, Vol. 17, pp. 1-7 (2006)

[Non-patent document 3] Jeffries T W et al., Applied Microbiology and Biotechnology, Vol. 63, pp. 495-509 (2004)

[Non-patent document 4] Bruinenberg P M et al., Applied Microbiology and Biotechnology, Vol. 18, pp. 287-292 (1983)

[Non-patent document 5] Koetter P et al., Applied Microbiology and Biotechnology, Vol. 38, pp. 776-783 (2004)

[Non-patent document 6] Deng X X et al., Applied Biochemistry and Biotechnology, Vol. 24/25, pp. 193-199 (1990)

[Non-patent document 7] Johansson B et al., Applied and Environmental Microbiology, Vol. 67, pp. 4249-4255 (2001)

[Non-patent document 8] Eliasson A et al., Enzyme and Microbial Technology, Vol. 29, pp. 288-297 (2001)

[Non-patent document 9] Jeppsson M et al., FEMS Yeast Research, Vol. 3, pp. 167-175 (2003)

[Non-patent document 10] Walfridsson M et al., Applied Microbiology and Biotechnology, Vol. 48, pp. 218-224 (1997)

[Non-patent document 11] Sedlak M et al., Applied Biochemistry and Biotechnology, Vol. 113-116, pp. 403-416 (2004)

[Non-patent document 12] Jin Y-S et al., Applied Microbiology and Biotechnology, Vol. 69, pp. 495-503 (2003)

DISCLOSURE OF THE INVENTION

Object to be Attained by the Invention

It has been impossible to efficiently produce ethanol from wood-based biomass by a conventional method. Thus, an effective method by which ethanol can be efficiently and inexpensively produced from a wood-based biomass resource has been desired. Major causes for this are: microorganisms that can use xylose richly contained in a saccharified solution of wood-based biomass are limited; microorganisms that highly efficiently convert xylose to ethanol have not been developed; and even conventional genetic recombinant microorganisms having xylose fermentability provided thereto are substantially unable to ferment xylose in the presence of glucose (fermentation is suppressed by glucose).

Therefore, the present invention provides a genetic recombinant yeast capable of producing high yields of ethanol from xylose and fermenting xylose even in the presence of glucose and an effective method for producing ethanol using the same.

Means for Attaining the Object

As a result of intensive studies to achieve the above objects, the present inventors have prepared a xylose metabolic system (XR, [wild-type or modified-type] XDH, and XK) expression cassette that can be efficiently integrated into a yeast chromosome, introduced the expression cassette into host yeast cells, and thus prepared a genetic recombinant yeast capable of highly efficiently producing ethanol from xylose.

Furthermore in the present invention, in addition to breeding via introduction of the above xylose metabolic system expression cassette into an appropriate host yeast strain such as S. cerevisiae, a host yeast strain that has acquired strong xylose fermentability was selected. This selection is important for effective production of ethanol from xylose. The reasons for this are as described below. Improvement in ethanol yield and improvement in ethanol productivity are important factors for the highly efficient industrial production of ethanol from xylose. These two factors are very important in high-capacity and low-cost industrial manipulation. Improvement in ethanol yield has an effect on raw-material cost. On the other hand, improvement in ethanol productivity is a critical element in the cost of bioprocess equipment. Yield and productivity can be separately considered in some cases, but the two should be taken into consideration for optimization of the overall process. Ethanol productivity depends on the specific rate of substrate (xylose) consumption. If improvement of the specific rate of xylose consumption is realized via the process, ethanol productivity at an acceptable cost can be achieved by suppressing the production of byproducts (xylitol, glycerol, and the like) at a minimum level. Under such state, it is desired to optimize both ethanol yield and ethanol productivity. Specifically, a yeast strain producing ethanol in a high yield and having a high xylose to ethanol fermentation rate is most suitable for practical use and industrialization. Furthermore, a general genetic recombinant yeast prepared by providing xylose fermentability thereto does not allow substantially fermentation of xylose in the presence of glucose (suppression of fermentation by glucose). Resolution of this issue is an object for industrialization. Therefore, in addition to a metabolic engineering technique that cancels suppression by glucose, selection of a yeast strain having a high glucose fermentation rate is also important for industrial xylose to ethanol fermentation.

For selection of yeast strains retaining in excellent xylose fermentability in the present invention, 5 types of yeast strain were selected as host yeast strains for genetic transformation. Specifically, the 5 types of yeast strain are experimental strains (the D452-2 strain and the INVSc1 strain) and industrial strains (the Type-II (bread yeast) strain, the IR-2 strain (FERM BP-754), and the shochu yeast No. 3 strain (Sake yeast kyokai No. 3)) (see FIG. 2). The D452-2 strain is a monoploid and the other 4 types of yeast (the INVSc1 strain, the Type-II strain, the IR-2 strain, and the shochu yeast No. 3 strain) are diploids. In addition, the IR-2 strain is an aggregating yeast known as a yeast strain that can continuously or repeatedly perform fermentation, and it is more suitable for practical use and industrialization (see JP Patent Publication (Kokai) No. 62-65679 A (1987)).

The above xylose metabolic system expression cassette was introduced into the 5 above types of host cell strain, and then genetic recombinant yeast capable of highly efficiently producing ethanol from xylose selected from among the strains. The present inventors have discovered that such genetic recombinant yeast can highly efficiently produce ethanol not only from xylose, but also from mixed sugar or a saccharified solution containing xylose, and thus they have completed the present invention.

Moreover, the present inventors have discovered that the xylose fermentability of genetic recombinant yeast (prepared by introducing the above xylose metabolic system expression cassette thereinto) can be improved by performing a series of acclimatization treatment steps for the genetic recombinant yeast in xylose-containing media. Thus, the present invention has been completed.

The present invention is as described below.

[1] A genetic recombinant yeast capable of highly efficiently producing ethanol from xylose, in which an XR gene, an XDH gene, and an XK gene are introduced by chromosomal integration.

[2] The genetic recombinant yeast according to [1], wherein the XR gene and the XDH gene are derived from a yeast.

[3] The genetic recombinant yeast according to [2], wherein the XR gene and the XDH gene are derived from a yeast selected from the group consisting of Candida Shehatae, Pichia stipitis, and Pachysolen tannophilus.

[4] The genetic recombinant yeast according to [3], wherein the XR gene and the XDH gene are derived from Pichia stipitis.

[5] The genetic recombinant yeast according to [1], wherein the XK gene is derived from a yeast or a bacterium.

[6] The genetic recombinant yeast according to [5], wherein the XK gene is derived from a yeast or a bacterium selected from the group consisting of Candida Shehatae, Pichia stipitis, Pachysolen tannophilus, Saccharomyces cerevisiae, Schizosaccharomyces pombe, and Escherichia coli.

[7] The genetic recombinant yeast according to [6], wherein the XK gene is derived from Saccharomyces cerevisiae.

[8] The genetic recombinant yeast according to [1], wherein the XR gene and the XDH gene are derived from Pichia stipitis and the XK gene is derived from Saccharomyces cerevisiae.

[9] The genetic recombinant yeast according to any one of [1] to [8], wherein the XR gene, the XDH gene, and the XK gene are constitutively expressed.

[10] The genetic recombinant yeast according to [9], wherein the XR gene, the XDH gene, and the XK gene are each expressed by a PGK promoter which constantly expresses each gene.

[11] The genetic recombinant yeast according to any one of [1] to [10], wherein the XDH gene encodes modified-type XDH (DNA disclosed as SEQ ID NO: 1, and protein diclosed as SEQ ID NO: 13) prepared by changing the coenzyme requirement to nicotinamide adenine dinucleotide phosphate ($NADP^+$) requirement.

[12] The genetic recombinant yeast according to any one of [1] to [11], wherein the XR gene, the XDH gene, and the XK gene are integrated into a single allele of a chromosomal DNA by homologous recombination, or are separately integrated onto different alleles of a chromosomal DNA by homologous recombination.

[13] The genetic recombinant yeast according to any one of [1] to [12], wherein the genetic recombinant yeast is prepared from Saccharomyces cerevisiae.

[14] A method for producing ethanol from xylose, which uses the genetic recombinant yeast according to any one of [1] to [13].

[15] A method for producing ethanol from a saccharified solution prepared from lignocellulose-based biomass, which uses the genetic recombinant yeast according to any one of [1] to [13].

[16] A method for improving the xylose fermentability of the genetic recombinant yeast according to any one of [1] to [13] by acclimatization treatment.

Effects of the Invention

The genetic recombinant yeast of the present invention can highly efficiently convert xylose to ethanol (having high a xylose fermentation rate and producing ethanol from xylose in high yields). Although xylose fermentation is generally inhibited in the presence of glucose, all genetic recombinant yeast strains of the present invention can perform co-fermentation of xylose even in the presence of glucose. In particular, when the hosts for the genetic recombinant yeast strains are industrial strains (the IR-2 strain (FERM BP-754) and the Type-II strain), xylose fermentation is accelerated in the presence of glucose. Furthermore, since xylose metabolic system (XR, XDH, and XK) genes are all efficiently introduced by chromosomal integration in the present invention, the expressions of the genes are more stable than those for which introduction is performed using plasmids. Also, the yeast strains can be directly grown not in auxotrophic minimal medium for retaining plasmids, but in nutrient-rich complete media or saccharified solutions, so that the growth rate and the rate of sugar metabolism are also increased. Actually, when a saccharified solution prepared from wood-based biomass was fermented using the genetic recombinant yeast of the present invention, not only a hexose such as glucose but also a pentose such as xylose could be efficiently converted to ethanol. In addition, even in the case of a recombinant yeast strain with relatively low xylose fermentability, the xylose fermentability can be significantly improved by a series of acclimatization treatment steps that involve subculture of the strain in xylose-containing media while applying selection pressure. Therefore, according to the present invention, xylose, which has been merely used as wood-based biomass can be highly efficiently converted to ethanol, which is expected to serve as a next-generation liquid energy source.

This description includes part or all of the contents as disclosed in the descriptions and/or drawings of Japanese Patent Application Nos. 2008-014080 and 2008-211274, which are priority documents of the present application.

BRIEF DESCRIPTION OF THE DRAWINGS

In FIG. 1, "XR" indicates "xylose reductase," "XDH" indicates "xylitol dehydrogenase," and "XK" indicates "xylulokinase." According to a conventional method, genes encoding Pichia stipitis-derived XR and XDH, respectively, and a gene encoding Saccharomyces cerevisiae-derived XK are introduced into yeast, so that a xylose-fermenting yeast is produced. The genetic recombinant yeast obtained by the conventional method is problematic in that the xylose to ethanol conversion efficiency is not so good since a comparable amount of xylitol is accumulated, and that xylose fermentation is suppressed in the presence of glucose. On the other hand, according to an embodiment of the present invention, an expression cassette of XR, wild-type or mutant XDH and XK is integrated into a yeast chromosome, and then the gene group is appropriately expressed within yeast, so that a plurality of hexose-pentose cofermenting yeast strains are prepared. From among the thus prepared yeast strains, yeast strains having high xylose fermentation rates and being capable of highly efficiently producing ethanol from xylose in high yields are selected. Accordingly, such hexose-pentose cofermenting yeast strains prepared according to the present invention has high xylose fermentability and can highly efficiently produce ethanol.

FIG. 3 shows the specific activity of enzymes (XR, XDH, and XK) expressed by the thus prepared genetic recombinant yeast.

FIG. 8 shows the results of batch fermentation experiments using xylose and mixed sugar containing xylose, whereby comparing xylose fermentability of genetic recombinant yeast strains and/or microorganisms reported to have relatively good xylose fermentability with the xylose fermentability of the R-ARSdR strain and the R-WT strain according to the present invention.

BEST MODE FOR CARRYING OUT THE INVENTION

XR is an enzyme that catalyzes a reaction for xylose to xylitol conversion. The XR gene is not particularly limited, as long as it is a gene encoding such enzyme, and is derived from yeast such as *Candida Shehatae, Pichia stipitis*, and *Pachysolen tannophilus*. Preferably, the XR gene is derived from *Pichia stipitis*.

XDH is an enzyme that catalyzes a reaction for xylitol to xylulose conversion. The XDH gene is not particularly limited, as long as it encodes such enzyme, and is derived from yeast such as *Candida Shehatae, Pichia stipitis*, and *Pachysolen tannophilus*. Preferably, the XDH gene is derived from *Pichia stipitis*.

XK is an enzyme that catalyzes a reaction for conversion of xylose and ATP to xylulose-5-phosphate and ADP. The XK gene is not particularly limited, as long as it encodes such enzyme and is derived from yeast or bacteria such as *Candida Shehatae, Pichia stipitis, Pachysolen tannophilus, Saccharomyces cerevisiae, Schizosaccaromyces pombe*, or *Escherichia coli*. Preferably, the XK gene is derived from *Saccharomyces cerevisiae*.

These genes can be obtained by a general method known by persons skilled in the art, such as a hybridization method and a PCR method.

Figure 1:
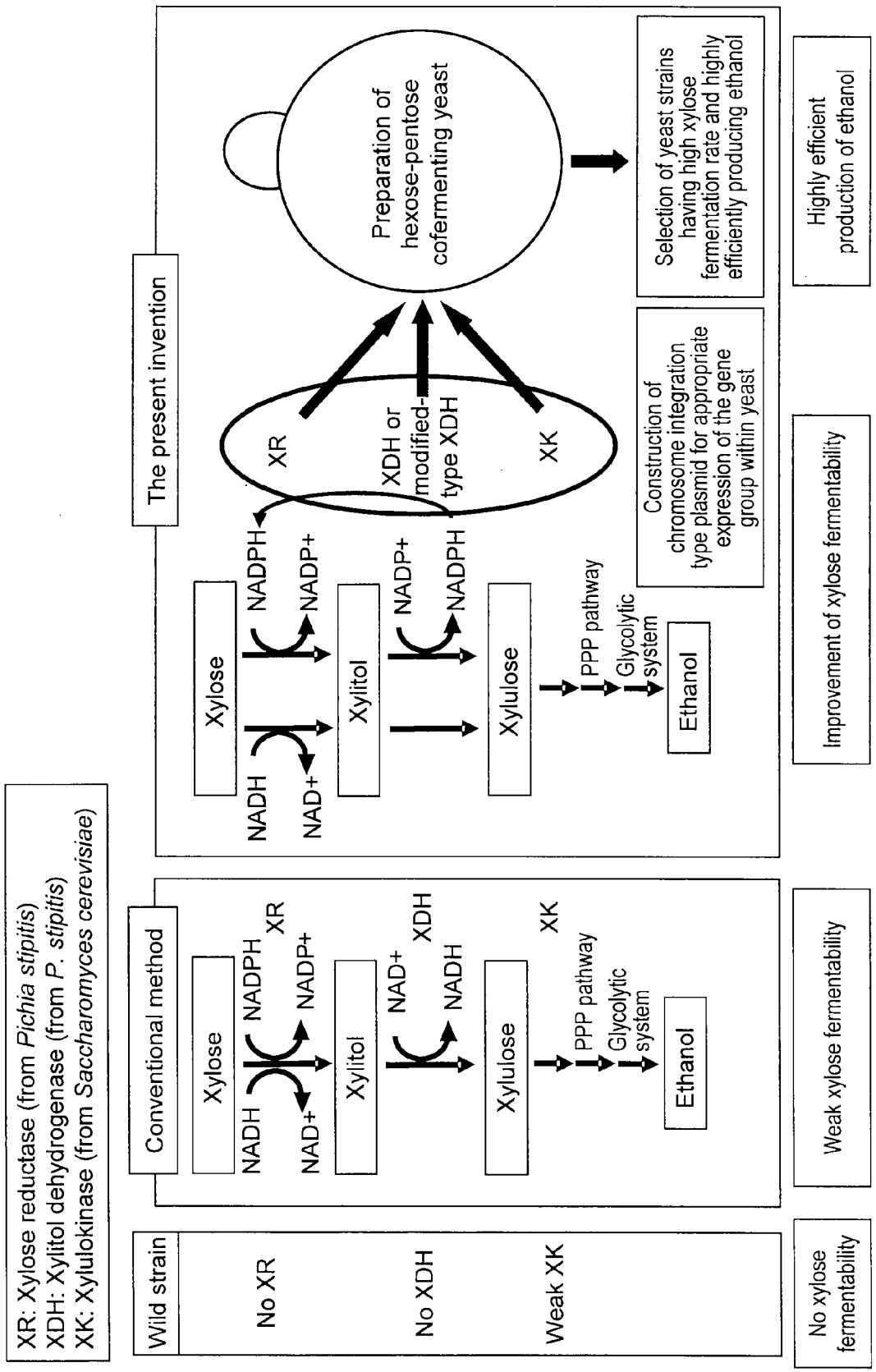
FIG. 1 is an explanatory diagram showing the xylose metabolic pathways within a yeast.

As XDH, a modified type thereof with a changed coenzyme requirement is desirably used. In the case of wild-type XDH, nicotinamide adenine dinucleotide ($NAD^+$) is generally used as a coenzyme. Meanwhile, in the case of "modified-type XDH" of the present invention, nicotinamide adenine dinucleotide phosphate ($NADP^+$) is used as a coenzyme. The amino acid sequence or the nucleotide sequence of the modified-type XDH is not particularly limited, as long as $NADP^+$ can be used as a coenzyme. The amino acid sequence is preferably a sequence prepared by substitution of at least one of amino acids corresponding to amino acids 207 to 211 of the amino acid sequence of XDH with another amino acid(s) such as alanine, arginine, serine, or threonine. Particularly preferable examples thereof include the amino acid sequence of XDH in which aspartic acid at position 207 is substituted with alanine, the same in which isoleucine at position 208 is substituted with arginine, the same in which phenylalanine at position 209 is substituted with serine or threonine, and the same in which asparagine at position 211 is substituted with arginine. Further preferable examples thereof include the amino acid sequence of XDH in which aspartic acid at position 207 is substituted with alanine, the same in which isoleucine at position 208 is substituted with arginine, the same in which phenylalanine at position 209 is substituted with serine, and the same in which asparagine at position 211 is substituted with arginine (DNA disclosed as SEQ ID NO: 1, and protein diclosed as SEQ ID NO: 13) (see Watanabe S. et al., The Journal of Biological Chemistry Vol. 280, No. 11, pp. 10340-10349 (2005)). The modified-type XDH uses $NADP^+$ as a coenzyme for conversion to NADPH. In contrast, XR uses NADPH mainly as a coenzyme for conversion to $NADP^+$. Hence, coenzyme supply balance is maintained and yeast in which the two genes have been introduced becomes possible to efficiently convert xylose to xylulose (see FIG. 1).

A modified-type enzyme can be prepared by a method known in the art such as random mutation and site-directed mutagenesis. In general, such random mutation method involves constructing an enzyme mutant pool using gene shuffling or error-prone PCR and then screening for a mutant modified to have a property of interest. Site-directed mutagenesis involves performing PCR using primers for XDH cloning, which have been designed based on the known XDH gene sequence and in which a mutation has been introduced into a predetermined position, so as to be able to introduce the mutation into the predetermined position in the cloned XDH gene.

The genes encoding these 3 types of enzyme are expressed within host cells. This can be performed by a general molecular biological technique known by persons skilled in the art (see Sambrook J. et al., "Molecular Cloning A LBORATORY MANUAL/second edition," Cold Spring Harbor Laboratory Press (1989)). Specifically, genes encoding the enzymes are incorporated into an appropriate vector and then an appropriate host organism is transformed with the vector, so that the genes can be expressed.

As a vector, a general yeast expression vector (for gene introduction and expression) known by persons skilled in the art can be used. As a vector to be used upon yeast introduction, any of a multi-copy type (YEp type), a single copy type (YCp type), and a chromosome integration type (YIp type) can be used. A chromosome integration type is preferably used.

A vector can contain, in addition to an enzyme gene of interest, a replication origin that enables replication in host cells, and a selection marker for identification of a transformant. A vector can further preferably contain an appropriate yeast-derived transcriptional or translation regulatory sequence. The replication origin, the selection marker, the regulatory sequence and the appropriate yeast-derived transcriptional or translation regulatory sequence are connected to the gene sequence of the enzyme if desired. Examples of such regulatory sequences include a transcription promoter, an operator, or an enhancer, a mRNA ribosome-binding site, and appropriate sequences that regulate the initiation and termination of transcription and translation. A transcription promoter that can be used herein is not particularly limited, as long as it can drive gene expression within host cells. Examples of such transcription promoter that can be used herein include a GAL1 promoter, a GAL10 promoter, a heat shock protein promoter, an MFα1 promoter, a PHO5 promoter, a PGK promoter, a GAP promoter, an ADH1 promoter, and an AOX1 promoter. The PGK promoter is preferably used. As a selection marker, a selection marker that is generally used can be used according to a conventional method. Examples thereof include genes involving resistance to antibiotics (e.g., tetracycline, ampicillin or kanamycin or neomycin, hygromycin, or spectinomycin) or auxotrophic genes such as HIS3 and TRP 1.

Figure 2:
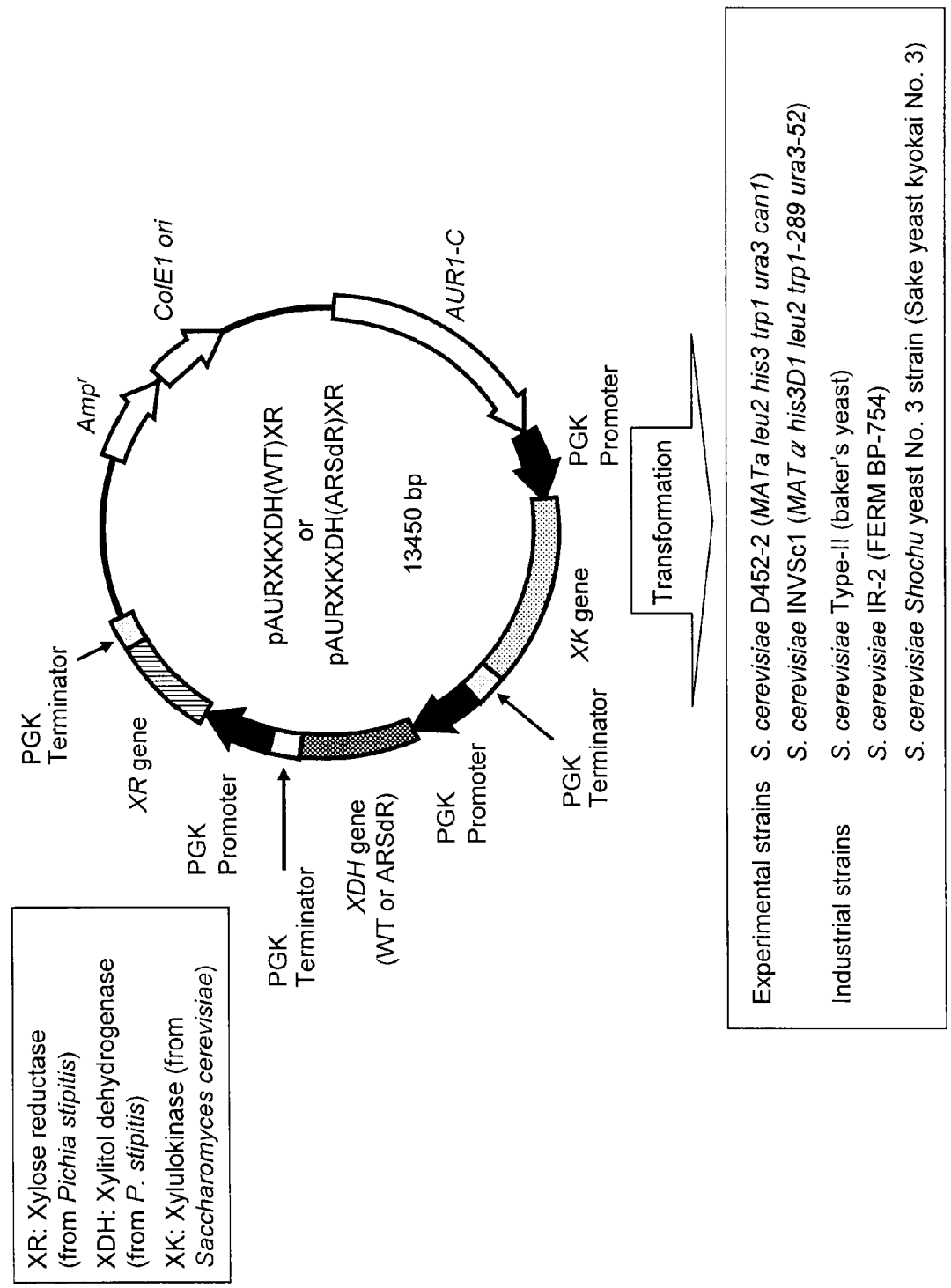
FIG. 2 shows yeast chromosome-integration plasmids (pAURXKXDH (WT) XR and pAURXKXDH (ARSdR) XR) and host yeast strains (the D452-2 strain, the INVSc1 strain, the Type-II strain, the IR-2 strain, and the shochu yeast No. 3 strain (Sake yeast kyokai No. 3)) for xylose metabolism, in order to prepare a genetic recombinant yeast.

Examples of yeast cells that can be used as host cells include, but are not particularly limited to, *Candida Shehatae, Pichia stipitis, Pachysolen tannophilus, Saccharomyces cerevisiae,* and *Schizosaccaromyces pombe. Saccharomyces cerevisiae* is particularly preferred herein. Further preferable examples thereof include experimental strains (the D452-2 strain and the INVSc1 strain) and industrial strains (the Type-II (bread yeast) strain, the IR-2 strain (FERM BP-754), and the shochu yeast No. 3 strain (Sake yeast kyokai No. 3) (see FIG. 2)). Particularly preferred examples thereof include the IR-2 strain (FERM BP-754) and the Type-II strain known as industrial strains.

The term "experimental strain" refers to a yeast strain that is used for conveniency in terms of experimentation. The term "industrial strain (practical strain)" refers to a yeast strain that is used for usefulness in terms of practical use. For example, yeast strains that are used for wine brewing, sake brewing, or shochu (distilled spirit) brewing are industrial strains. Since bread yeast strains are used in the laboratory, they are experimental strains in that context. Genotypes of experimental strains are known. Hence in most cases, a plasmid containing an auxotrophic selection marker gene is introduced or an auxotrophic gene is mutated so that an auxotrophic expression cassette can be integrated into a chromosome. On the other hand, since no auxotrophic gene is mutated in industrial strains, it is impossible to directly introduce a plasmid carrying an auxotrophic marker gene or directly integrate an auxotrophic expression cassette into a chromosome. Moreover, since experimental strains are often used for conjugation experiments or sporulation experiments, most of them are monoploids. Most industrial strains are multi-ploids such as diploids or tetraploids.

Examples of a method for introducing a vector into host cells include a calcium phosphate method or a calcium chloride/rubidium chloride method, an electroporation method, an electroinjection method, a method involving chemical treatment such as PEG, and a method using a gene gun or the like.

The vector of the present invention may contain an auxotrophic expression cassette or a drug resistant expression cassette and preferably contains a drug-resistant expression cassette. When such drug-resistant expression cassette is used, a genetic recombinant yeast can be cultured even in a complete medium such as YPD; and then the growth rate of the genetic recombinant yeast can be greatly increased compared with a yeast containing an auxotrophic expression cassette introduced therein, which must be cultured in a minimal medium supplemented with amino acid and the like. Furthermore, the use of such drug-resistant expression cassette has an advantage such that direct chromosomal integration into a practical strain is possible without the need of disrupting any yeast auxotrophic gene.

Preferably in the present invention, XR, XDH, and XK are constitutively expressed. For example, after introduction of the XR, XDH, and XK genes into a chromosomal integration-type vector or the like, the vector is integrated into a yeast chromosome, and then single or several copies of the genes are preferably expressed. These genes may be integrated by homologous recombination into a single allele of a chromosomal DNA. Alternatively, these genes may be separately integrated by homologous recombination into different alleles of a chromosomal DNA. Preferably, the 3 types of enzyme gene are simultaneously integrated into a single allele of a host DNA.

The genetic recombinant yeast according to the present invention can produce ethanol from xylose by fermentation reaction. At this time, the concentration of xylose contained in a medium ranges from 0.1% to 20%, preferably ranges from 0.5% to 10%, and is further preferably 4.5%. The concentration of glucose contained in a medium ranges from 0.1% to 20%, preferably ranges from 0.5% to 10%, and is further preferably 4.5%.

Also, the genetic recombinant yeast according to the present invention can produce ethanol from a saccharified solution prepared from lignocellulose-based biomass by fermentation reaction. Such saccharified solution can be prepared from a woody material (particularly broad-leaved tree rich in xylan) or a material from lignocellulose-based biomass such as agricultural waste. However, examples thereof are not particularly limited to them. As a saccharification technique for preparation of such saccharified solution, a technique generally used in the art can be used. Such saccharification technique may be either an acid digestion method or an enzymatic saccharification technique. A preferable example thereof is a non-sulfuric acid pretreatment•enzymatic saccharification technique from which high efficiency and low environmental burden can be expected. Actually, when fermentation is performed using yeast, an undetoxified saccharified solution may be directly used or a detoxified saccharified solution may be used. Regarding the pH of such saccharified solution, an untreated acid saccharified solution may be used or used after adjustment to around neutrality. Preferably, the saccharified solution is adjusted to around neutrality and then used. Such saccharified solution may or may not be supplemented with a yeast extract or a nutritional source such as peptone. Preferably, such saccharified solution is supplemented with a 1% yeast extract.

The above fermentation reaction can be performed by a general method known by persons skilled in the art. The temperature for culture is controlled to range from 25° C. to 38° C., preferably controlled to range from 27° C. to 33° C., and further preferably controlled at 30° C. The pH of the medium is controlled to range from 3.0 to 7.6, preferably controlled to range from 5.0 to 6.0, and further preferably controlled at 5.5. Fermentation proceeds under anaerobic conditions. That is, conditions in which no oxygen is present are required. Accordingly, a step of removing oxygen within the system or dissolved oxygen in the medium before fermentation (that is, a step of infusion of nitrogen gas into the medium) is preferably performed. Either continuous-type or batch-type reaction may be performed.

A medium at 0 to 192 hours, preferably 0 to 96 hours, further preferably 48 hours after the start of culture is recovered and then ethanol is separated. As a method for separation of ethanol from a medium, a known method such as distillation or pervaporation membrane is employed. Preferably a method that involves distillation is employed. Subsequently, the thus separated ethanol is further purified (as an ethanol purification method, a known method such as distillation can be employed), so that ethanol can be obtained.

The xylose fermentability of the genetic recombinant yeast according to the present invention can be significantly improved by subjecting the yeast to acclimatization treatment for xylose fermentability. Such acclimatization treatment for xylose fermentability is performed through subculture of the yeast in a minimal medium containing xylose while applying selection pressure. At this time, the concentration of xylose contained in such medium ranges from 0.1% to 20%, preferably ranges from 0.5% to 10%, and is further preferably 3%. The concentration of glucose contained in such medium ranges from 0.01% to 20%, preferably ranges from 0.05% to 10%, and is further preferably 0.1%. The temperature for culture is controlled to range from 25° C. to 38° C., preferably controlled to range from 27° C. to 33° C., and further preferably controlled at 30° C. The pH for such medium is controlled to range from 3.0 to 7.6, preferably controlled to range from 5.0 to 6.0, and further preferably controlled at 5.5. The time for a single culture ranges from 24 hours to 120 hours, preferably ranges from 48 hours to 94 hours, and is further preferably 72 hours. The number of passage ranges from 1 passage to 20 passages, preferably ranges from 5 passages to 15 passages, and is further preferably 10 passages. Culture may be performed either anaerobically or microaerobically and preferably performed anaerobically. In the case of anaerobic conditions, the step of infusion of nitrogen gas into a medium is preferably performed as described above. Either continuous-type or batch-type reaction may be performed.

EXAMPLES

Hereafter, the present invention is described in detail with reference to Examples below, although the present invention is not limited thereto.

Example 1

Preparation of pBS-PGK-XR-PGK

For preparation of a wild-type XR gene, the following two primers were designed in reference to the *Pichia stipitis* XR gene registered at GeneBank (Registration No. XM_001385144) (DNA disclosed as SEQ ID NO: 2, and protein diclosed as SEQ ID NO: 14). In addition, a BamH I recognition site was added to the 5' terminal portion of the XR gene to prepare a primer and an Hind III recognition site was added to the 3' terminal portion of the XR gene to prepare the other primer.

```
                                          (SEQ ID NO: 3)
5'-GCATaagcttATGCCTTCTATTAAGTTGAACTCTGG-3'

(SEQ ID NO: 4)
5'-TAAggatccTTAGACGAAGGATAGGAATCTTGTCC-3'
```

PCR was carried out using Blend Taq DNA polymerase (Toyobo Co., Ltd.). With the use of primers (10 pmol each) and 100 ng of *P. stipitis* genomic DNA, the XR gene was amplified under conditions involving a denaturation reaction at 94° C. for 30 seconds, an annealing reaction at 55° C. for 30 seconds, and an extension reaction at 72° C. for 1 minute. The thus obtained DNA fragment was introduced into the Hind III and BamH I restriction enzyme cleavage sites of plasmid pBluescript II KS(+) (Stratagene) and the resultant was designated pBS-XR. Subsequently, for ligation of a PGK promoter to a site upstream of the XR gene, a PGK promoter fragment obtained by cleavage of pPGK with Xho I and Hind III was introduced into Xho I and Hind III restriction enzyme cleavage sites of pBS-XR. The resultant was designated pBS-PGK-XR. Furthermore, for addition of a sequence recognizing Xho I and Spe I cleavage sites to the 3' end of a PGK terminator to be ligated downstream of the XR gene, the following two primers were designed. In addition, a BamH I recognition site was added to the 5' terminal portion the PGK terminator gene to prepare a primer and Xho I and Spe I recognition sites were added to the 3' terminal portion of the PGK terminator gene to prepare the other primer.

```
                                          (SEQ ID NO: 5)
5'-CCCggatccGGGAAATAAATTGAATTGAATTGAAATCG-3'

(SEQ ID NO: 6)
5'-GACactagtctcgagCAGCTTTAACGAACGCAGAATTTTCG-3'
```

PCR was carried out using Blend Taq DNA polymerase (Toyobo Co., Ltd.). With the use of primers (10 pmol each) and 100 ng of pPGK plasmid DNA, a PGK terminator gene was amplified under conditions involving a denaturation reaction at 94° C. for 30 seconds, an annealing reaction at 55° C. for 30 seconds, and an extension reaction at 72° C. for 1 minute. The thus obtained DNA fragment was introduced into the BamH I and Spe I restriction enzyme cleavage sites of pBS-PGK-XR. The resultant was designated pBS-PGK-XR-PGK.

Example 2

Preparation of pPGK-XDH (WT)

For preparation of a wild-type XDH gene, the following two primers were designed in reference to the *Pichia stipitis* XDH gene registered at GeneBank (Registration No. AF127801 or X55392) (DNA disclosed as SEQ ID NO: 7, and protein diclosed as SEQ ID NO: 15). In addition, an EcoR I recognition site was added to the 5' terminal portion of the XDH gene to prepare a primer and a BamH I recognition site was added to the 3' terminal portion of the XDH gene to prepare the other primer.

```
                                          (SEQ ID NO: 8)
5'-CATgaattcATGACTGCTAACCCTTCCTTGGTG-3'

(SEQ ID NO: 9)
5'-TAAggatccTTACTCAGGGCCGTCAATGAGAC-3'
```

PCR was carried out using Blend Taq DNA polymerase (Toyobo Co., Ltd.). With the use of primers (10 pmol each)

and 100 ng of *P. stipitis* genomic DNA, the XDH gene was amplified under conditions involving a denaturation reaction at 94° C. for 30 seconds, an annealing reaction at 60° C. for 30 seconds, and an extension reaction at 72° C. for one minute and 30 seconds. The thus obtained DNA fragment was introduced into EcoR I and BamH I restriction enzyme cleavage sites of plasmid pPGK. The resultant was designated pPGK-XDH (WT).

Example 3

Construction of pPGK-XK

For preparation of a wild-type XK gene, the following two primers were designed in reference to the *Saccharomyces cerevisiae* XK gene registered at GeneBank (NC_001139.7) (DNA disclosed as SEQ ID NO: 10, and protein diclosed as SEQ ID NO: 16). In addition, an EcoR I recognition site was added to the 5' terminal portion of the XK gene to prepare a primer and a BamH I recognition site was added to the 3' terminal portion to prepare the other primer.

(SEQ ID NO: 11)
5'-CATgaattcATGTTGTGTTCAGTAATTCAGAGACAGAC-3'

(SEQ ID NO: 12)
5'-TAAggatccTTAGATGAGAGTCTTTTCCAGTTCGC-3'

PCR was carried out using Blend Taq DNA polymerase (Toyobo Co., Ltd.). With the use of primers (10 pmol each) and 100 ng of *S. cerevisiae* genomic DNA, the XK gene was amplified under conditions involving a denaturation reaction at 94° C. for 30 seconds, an annealing reaction at 54° C. for 30 seconds, and an extension reaction at 72° C. for 2 minutes. The thus obtained DNA fragment was introduced into the EcoR I and BamH I restriction enzyme cleavage sites of plasmid pPGK. The resultant was designated pPGK-XK.

Example 4

Construction of pAURXK

For introduction of an XK fragment with a PGK promoter and a PGK terminator into a chromosomal integration-type plasmid pAUR101 (Takara Bio Inc.), the pPGK-XK plasmid constructed in Example 3 was cleaved with Xho I and Sal I and then the XK fragment with the PGK promoter and the PGK terminator was introduced into the Sal I site of pAUR101. For this, pAUR101 cleaved with Sal I was subjected to alkaline phosphatase treatment so as to remove phosphate groups on cleavage surfaces. The thus obtained plasmid was cleaved with a restriction enzyme and then the electrophoresis pattern was examined, so as to confirm the direction in which the XK fragment with the PGK promoter and the PGK terminator had been incorporated into pAUR101. A plasmid in which the fragment had been introduced into the forward direction with respect to that of the AUR1-C gene was designated pAURXK.

Example 5

Construction of pAURXKXDH (WT)

For introduction of a wild-type XDH fragment with a PGK promoter and a PGK terminator into the pAURXK plasmid constructed in Example 4, the plasmid pPGK-XDH (WT) constructed in Example 2 was cleaved with Xho I and Sal I and then the wild-type XDH fragment with the PGK promoter and the PGK terminator was introduced into the Sal I site of pAURXK. For this, pAURXK cleaved with Sal I was subjected to alkaline phosphatase treatment, so as to remove phosphate groups on the cleavage surfaces. The thus obtained plasmid was cleaved with a restriction enzyme and then the electrophoresis pattern was examined, so as to confirm the direction in which the wild-type XDH fragment with the PGK promoter and the PGK terminator had been incorporated into pAURXK. A plasmid in which the fragment had been introduced into the forward direction with respect to that of the AUR1-C gene was designated pAURXKXDH (WT).

Example 6

Construction of pAURXKXDH (ARSdR)

For introduction of a modified-type XDH fragment with a PGK promoter and a PGK terminator into the pAURXK plasmid constructed in Example 4, a pPGK-XDH (ARSdR) plasmid (distributed by Professor Keisuke Makino, Bioenergy Research Section, Advanced Energy Utilization Division, Institute of Advanced Energy, Kyoto University) constructed by introducing modified-type XDH prepared by an enzyme engineering technique into pPGK was cleaved with Xho I and Sal I. The modified-type XDH fragment with the PGK promoter and the PGK terminator was introduced into the Sal I site of pAURXK. For this, pAURXK cleaved with Sal I was subjected to alkaline phosphatase treatment, so as to remove phosphate groups on the cleavage surfaces. The thus obtained plasmid was cleaved with a restriction enzyme and then the electrophoresis pattern was examined, so as to confirm the direction in which the modified-type XDH fragment with the PGK promoter and the PGK terminator had been incorporated into pAURXK. A plasmid in which the fragment had been introduced into the forward direction with respect to that of the AUR1-C gene was designated pAURXKXDH (ARSdR).

Example 7

Construction of pAURXKXDH (WT) XR

For introduction of an XR fragment with a PGK promoter and a PGK terminator into the pAURXKXDH (WT) plasmid constructed in Example 5, the pBS-PGK-XR-PGK plasmid constructed in Example 1 was cleaved with Xho I and then the XR fragment with the PGK promoter and the PGK terminator was introduced into a Sal I site of pAURXKXDH (WT). For this, pAURXKXDH (WT) cleaved with Sal I was subjected to alkaline phosphatase treatment, so as to remove phosphate groups on the cleavage surfaces. The thus obtained plasmid was cleaved with a restriction enzyme and then the electrophoresis pattern was examined, so as to confirm the direction in which the XR fragment with the PGK promoter and the PGK terminator had been incorporated into pAURXKXDH (WT). A plasmid in which the fragment had been introduced into the forward direction with respect to that of the AUR1-C gene was designated pAURXKXDH (WT) XR (see FIG. 2).

Example 8

Construction of pAURXKXDH (ARSdR) XR

For introduction of an XR fragment with a PGK promoter and a PGK terminator into the pAURXKXDH (ARSdR) plasmid constructed in Example 6, the pBS-PGK-XR-PGK plasmid constructed in Example 1 was cleaved with Xho I and then the XR fragment with the PGK promoter and the PGK terminator was introduced into a Sal I site of pAURXKXDH (ARSdR). For this, pAURXKXDH (ARSdR) cleaved with Sal I was subjected to alkaline phosphatase treatment, so as to remove phosphate groups on the cleavage surfaces. The thus obtained plasmid was cleaved with a restriction enzyme and then the electrophoresis pattern was examined, so as to confirm the direction in which the XR fragment with the PGK promoter and the PGK terminator had been incorporated into pAURXKXDH (ARSdR). A plasmid in which the fragment had been introduced into the forward direction with respect to that of the AUR1-C gene was designated pAURXKXDH (ARSdR) XR (see FIG. 2).

Example 9

Preparation of Genetic Recombinant Yeast Strain

As host cell strains, the D452-2 strain and the INVSc1 strain, which are experimental strains and the Type-II strain, the IR-2 strain, and the shochu yeast No. 3 strain, which are industrial strains were used. The D452-2 strain was distributed by the group of Professor Keisuke Makino, Bioenergy Research Section, Advanced Energy Utilization Division, Institute of Advanced Energy, Kyoto University. INVSc1 was purchased from Invitrogen. The Type-II strain was purchased from SIGMA. IR-2 (FERM BP-754) was obtained from the Deposition Center, National Institute of Advanced Industrial Science and Technology. Shochu yeast No. 3 was obtained from the Brewing Society of Japan. The pAURXKXDH (WT) XR plasmid constructed in Example 7 was transformed by a lithium acetate method using a YEASTMAKER yeast transformation system 2 (Clontech) into the D452-2 strain, the INVSc1 strain, the Type-II strain, the IR-2 strain, and the shochu yeast No. 3 strain. Thus, genetic recombinant yeast strains, a D-WT strain, an N-WT strain, a T-WT strain, an R-WT strain, and an S-WT strain were prepared. Also, the pAURXKXDH (ARSdR) XR plasmid constructed in Example 8 was transformed by a lithium acetate method using a YEASTMAKER yeast transformation system 2 (Clontech) into experimental yeast strains (the D452-2 strain and the INVSc1 strain) and industrial strains (the Type-II strain and the IR-2 strain). Thus, genetic recombinant yeast strains (a D-ARSdR strain, an N-ARSdR strain, a T-ARSdR strain, and an R-ARSdR strain) were prepared. Meanwhile, the D452-2 strain, the INVSc1 strain, the Type-II strain, and the IR-2 strain were transformed with a pAUR101 vector plasmid containing no enzyme gene, so that a D-Control strain, an N-Control strain, a T-Control strain, and an R-Control strain were prepared and used as control strains. In addition, for integration of pAURXKXDH (WT) XR, pAURXKXDH (ARSdR) XR, and pAUR101 into the chromosomes of such yeast strains, these plasmids were all cleaved with BsiW I to prepare linear plasmids and then transformed into such yeast strains.

Example 10

Enzyme-Specific Activity Determination

XR activity was determined by monitoring at 30° C. a decrease in absorbance at 340 nm specific to NAD(P)H to be generated by reaction. The amount required for generation of 1 μmol of NAD(P)$^+$ within 1 minute in a 50 mM phosphate buffer (900 μl) containing 200 mM xylose and 100 μl of 1.5 mM NAD(P)H was defined as one unit of XR.

XDH activity was determined by monitoring at 35° C. an increase in absorbance at 340 nm specific to NAD(P)$^+$ to be generated by reaction. The amount required for generation of 1 μmol of NAD(P)H within 1 minute in a 50 mM Tris-HCl buffer (900 μl) containing 50 mM MgCl$_2$, 300 mM xylitol, and 100 μl of 10 mM NAD(P)$^+$ was defined as one unit of XDH.

XK activity was determined by monitoring a decrease in absorbance at 340 nm specific to NADH to be generated by a reaction of a combination of pyruvate kinase (PK) and lactate dehydrogenase (LDH) using ADP to be generated upon conversion of xylulose to xylulose-5-phosphate. The amount required for generation of 1 μmol of NAD$^+$ within 1 minute in a 100 mM Tris-HCl buffer (900 μl) containing 2 mM MgCl$_2$, 8 mM NaF, 2 mM ATP, 0.2 mM phosphoenolpyruvate, 3 mM reduced glutathione, 10 U LDH, 10 U PK, 0.2 mM NADH, and 8.5 mM xylulose was defined as one unit of XK.

For determination of enzyme activity, xylose-fermenting yeast strains (the D-WT strain, the D-ARSdR strain, the N-WT strain, the N-ARSdR strain, the T-WT strain, the T-ARSdR strain, the R-WT strain, and the R-ARSdR strain) and the control yeast strains (the D-Control strain, the N-Control strain, the T-Control strain, and the R-Control) were aerobically cultured in complete media (20 g/l polypeptone, 10 g/l yeast extract: YPD medium) containing 20 g/l glucose at 30° C. for 48 hours. After cells were collected by centrifugation, each resultant was washed with sterile water and then suspended in an appropriate amount of a yeast protein extraction reagent Y-PER (Pierce). The cell suspension was stirred with a voltex mixer for 20 minutes and then centrifuged. The supernatant was used as a cell-free (protein) yeast extract for determination of enzyme activity.

Protein concentrations were determined using a Micro-BCA kit (Pierce). FIG. 3 shows the results of determination of enzyme specific activity. The specific activity of XR in xylose-fermenting yeast strains (the D-WT strain, the D-ARSdR strain, the N-WT strain, the N-ARSdR strain, the T-WT strain, the T-ARSdR strain, the R-WT strain, and the R-ARSdR strain) was extremely higher than that in all the control yeast strains (the D-Control strain, the N-Control strain, the T-Control strain, and the R-Control strain). Also, the specific activity of XDH in yeast strains expressing wild-type XDH (the D-WT strain, the N-WT strain, the T-WT strain, and the R-WT strain) was extremely high to NAD$^+$. In contrary, the specific activity of XDH in the modified-type XDH-expressing yeast strains (the D-ARSdR strain, the N-ARSdR strain, the T-ARSdR strain, and the R-ARSdR strain) was high to NADP$^+$. Moreover, the specific activity of XK in xylose-fermenting yeast was about twice as high as that in the control yeast.

Also, the specific activity of XR was 1.5 or more times higher in the T-WT strain and 5.5 or more times higher in the R-WT strain, when compared with the D-WT strain and the N-WT strain. Also when compared with the D-ARSdR strain and the N-ARSdR strain, the specific activity of XR was 1.3 or more times higher in the T-ARSdR strain and 6.9 or more times higher in the R-ARSdR strain. Overall, the specific activity of XR could be confirmed to tend to be higher in the ARSdR strain than in the WT strains.

On the other hand, the specific activity of XDH specific to NAD$^+$ was about 1.5 times higher in the N-WT strain and about 2.0 times higher in the R-WT strain when compared with the D-WT strain and the T-WT strain. In contrast, the specific activity of XDH specific to NADP was lower in the T-ARSdR strain and about 1.7 times higher in the N-WT strain when compared with the D-ARSdR strain and the R-WT strain. Compared with the specific activity of XDH specific to NAD⁺ in yeast expressing wild-type XDH, the specific activity of XDH specific to NADP⁺ in yeast expressing modified-type XDH was not so high. However, it was confirmed that when a cell-free (protein) yeast extract (extracted from a yeast strain cultured in a complete medium (20 g/l polypeptone, and 10 g/l yeast extract: YPX medium) containing 20 g/l xylose instead of glucose) was used, the specific activity of XDH specific to NADP⁺ was increased.

No significant difference was found among xylose-fermenting yeast strains in terms of the specific activity of XK. In any event, it was suggested that in the yeast strain, the xylose metabolic enzyme gene group was appropriately expressed at high levels within yeast.

Example 11

Culture of Genetic Recombinant Yeast

For an ethanol fermentation experiment, xylose-fermenting yeast strains (the D-WT strain, D-ARSdR strain, N-WT strain, N-ARSdR strain, T-WT strain, T-ARSdR strain, R-WT strain, and R-ARSdR strain) were cultured aerobically in complete media (20 g/l polypeptone, 10 g/l yeast extract: YPD medium or YPX medium) containing 20 g/l glucose or 20 g/l xylose at 30° C. for 48 hours. Yeast cells were collected by centrifugation, washed with sterile water, and then seeded in an appropriate amount in 20 ml of each fermentation medium (a complete medium [YPX medium] containing 45 g/l xylose, or a complete medium [YPDX medium] containing 45 g/l glucose and 45 g/l xylose, or a complete medium [YPDX2 medium] containing 25 g/l glucose and 15 g/l xylose) (the amounts of cells seeded were the same). Fermentation solutions were anaerobically cultured at 30° C. in 50-ml sealed vials with stirrers therein while gently stirring the solutions.

Example 12

Measurement of Ethanol Concentration

Concentrations of ethanol, glucose, xylose, xylitol, and other byproducts were measured by high performance liquid chromatography (HPLC; JASCO Corporation). An HPX-87H column (Bio-Rad) was used as a separation column. An HPLC apparatus was operated at 65° C. while applying 5 mM $H_2SO_4$ at a flow rate of 0.6 ml/min. Yeast growth was observed by measuring wavelength at 600 nm using a U-3000 spectrophotometer (Hitachi, Ltd.).

As a result of analysis, no significant difference in growth rate was observed among the D-WT strain, the D-ARSdR strain, the N-WT strain, the N-ARSdR strain, the T-WT strain, and the T-ARSdR strain. In contrast, the R-WT strain and the R-ARSdR strain were found to have growth rates extremely higher than the aforementioned yeast strains and exerted increased cell yields (about 1.5 times as great). Also, when glucose is present in media (YPDX media), compared with the D-WT strain, the D-ARSdR strain, the N-WT strain, and the N-ARSdR strain, the T-WT strain and the T-ARSdR strain were found to have somewhat increased growth rates, but not greater than the R-WT strain and the R-ARSdR strain, and they exhibited slightly increased cell yields.

Figure 4:
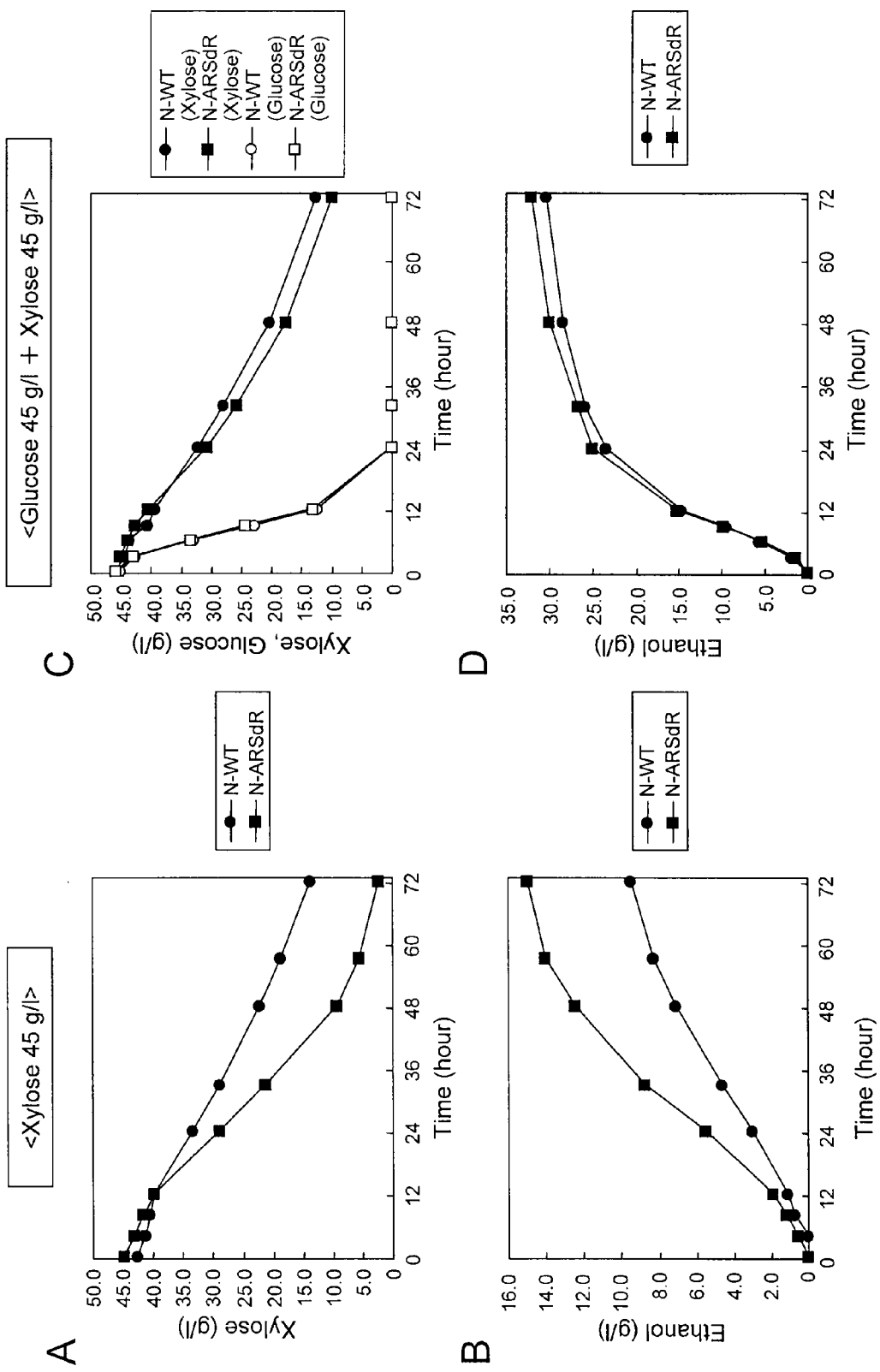
FIG. 4 shows the anaerobic ethanol fermentability (xylose consumption and ethanol concentration in YPX medium) of genetic recombinant yeast strains (the N-WT strain and the N-ARSdR strain) prepared using the INVSc1 strain as a host and the anaerobic ethanol fermentability (xylose and glucose consumption and ethanol production in YPDX media) of the same.

FIG. 4 shows xylose consumption (see FIG. 4A), xylose consumption and glucose consumption (see FIG. 4C), and ethanol production (see FIGS. 4B and D) with time in the N-WT strain and the N-ARSdR strain as a result of anaerobic culture of genetic recombinant yeast strains (the N-WT strain and N-ARSdR strain prepared using INVSc1 as a host) in media containing xylose alone (YPX media) (see FIGS. 4A and B) and mixed sugar media containing glucose and xylose (YPDX media) (see FIGS. 4C and D). In YPX media, whereas the N-WT strain consumed 68% of the total xylose after 72 hours, the N-ARSdR strain consumed 95% of the total xylose after 72 hours. The xylose consumption rate of the N-ARSdR strain was significantly higher than that of the N-WT strain (see FIG. 4A). Furthermore, in YPX media, whereas the N-WT strain produced 9.5 g/l ethanol after 72 hours, the N-ARSdR strain produced 14.9 g/l ethanol after 72 hours. The ethanol production rate of the N-ARSdR strain was significantly higher than that of the N-WT strain (see FIG. 4B). Regarding ethanol yield from the total xylose consumption, the ethanol yield of the N-WT strain was 65%, and that of the N-ARSdR strain was 69%. The ethanol yield of the N-ARSdR strain was higher than that of the N-WT strain. Meanwhile, in YPDX media, both the N-WT strain and the N-ARSdR strain completely consumed glucose within 24 hours (see FIG. 4C). Also, whereas the N-WT strain consumed 72% of the total xylose after 72 hours, the N-ARSdR strain consumed 78% of the total xylose after 72 hours. The xylose consumption rate of the N-ARSdR strain was slightly higher than that of the N-WT strain (see FIG. 4C). As such, the xylose consumption rate of the N-ARSdR strain could be confirmed to tend to increase in media containing xylose alone (YPX media) in comparison with the rate in the presence of glucose (YPDX media). However, xylose consumption rate in the N-WT strain was found to remain almost unchanged (FIG. 4A was compared with C). In YPDX media, also regarding ethanol production rate, difference in the ethanol production rate between the N-WT strain and the N-ARSdR strain was decreased, but the ethanol production rate of the N-ARSdR strain was higher than that of the N-WT strain (FIG. 4B was compared with D). Specifically, in YPDX media, whereas the N-WT strain produced 30.3 g/l ethanol after 72 hours, the N-ARSdR strain produced 32.0 g/l ethanol after 72 hours (see FIG. 4D). Regarding ethanol yield from the total sugar (glucose+xylose) consumption, the ethanol yield of the N-WT strain was 75% and that of the N-ARSdR strain was 77%. The ethanol yield of the N-ARSdR strain was higher than that of the N-WT strain. Furthermore, ethanol yields of all the yeast strains were higher in YPDX media than those in YPX media. More surprisingly, xylose consumption rate was lower than glucose consumption rate, but xylose was consumed even during glucose consumption (0 to 24 hours) (see FIG. 4C), suggesting almost no effects of glucose suppression. Similar results could be obtained for the D-WT strain and the D-ARSdR strain.

Figure 5:
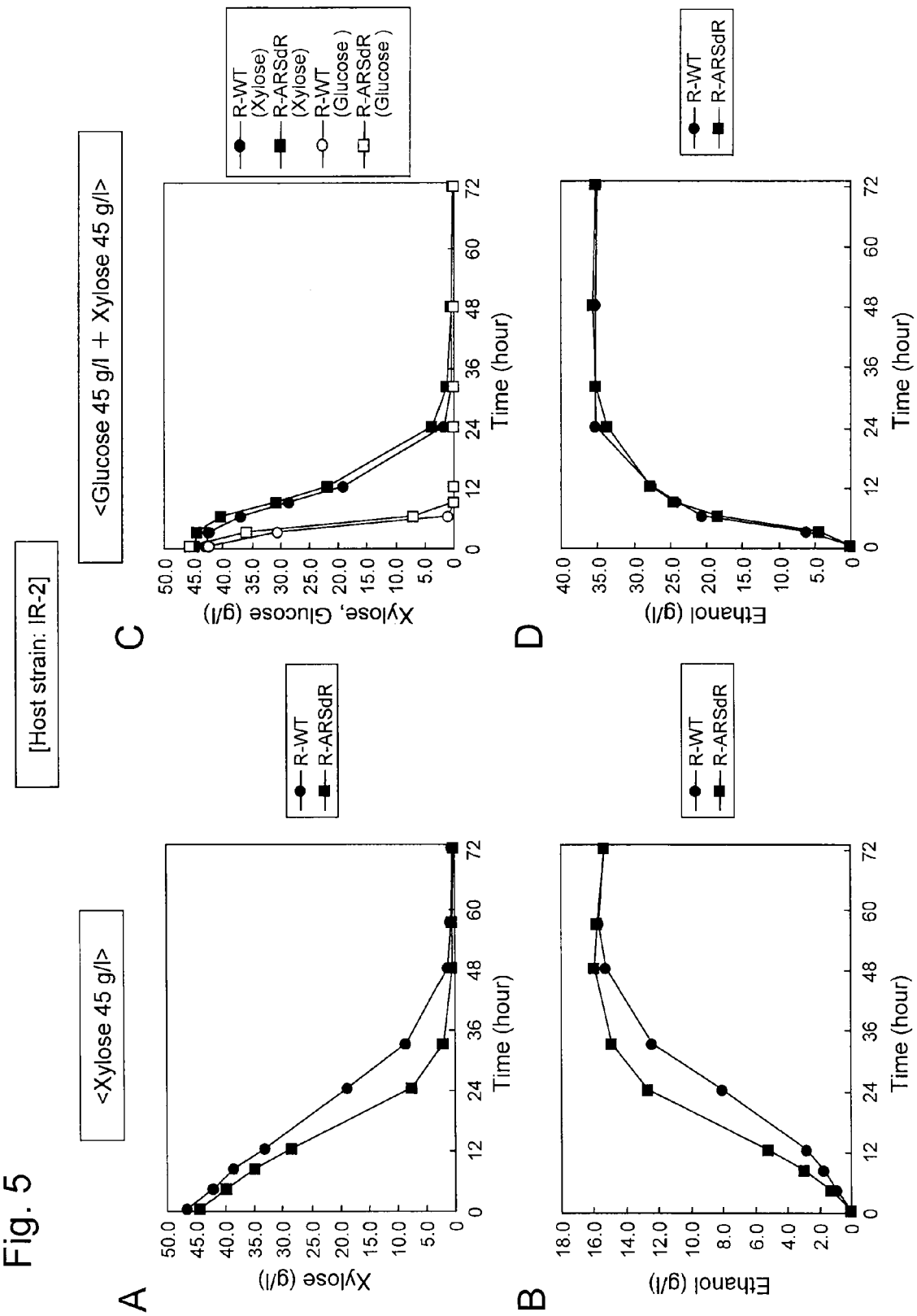
FIG. 5 shows the anaerobic ethanol fermentability (xylose consumption and ethanol concentration in YPX media) of genetic recombinant yeast strains (the R-WT strain and the R-ARSdR strain) prepared using the IR-2 strain as a host and the anaerobic ethanol fermentability (xylose and glucose consumption and ethanol production in YPDX media) of the same.

FIG. 5 shows xylose consumption (see FIG. 5A), xylose consumption and glucose consumption (see FIG. 5C), and ethanol production (see FIGS. 5B and D) with time of the R-WT strain and the R-ARSdR strain as a result of anaerobic culture of genetic recombinant yeast strains (the R-WT strain and the R-ARSdR strain prepared using IR-2 as a host) in media containing xylose alone (YPX media) (see FIGS. 5A and B) and mixed sugar media containing glucose and xylose (YPDX media) (see FIGS. 5C and D). In YPX media, whereas the R-WT strain consumed 82% of the total xylose after 33 hours, the R-ARSdR strain consumed 96% of the total xylose after 33 hours. Similar to the result of the N-WT strain and the N-ARSdR strain in FIG. 4A, the xylose consumption rate of the R-ARSdR strain was significantly higher than that of the R-WT strain (see FIG. 5A). Both the R-WT strain and the R-ARSdR strain consumed xylose almost completely within 48 hours. Moreover in YPX media, whereas the R-WT strain produced 12.4 g/l ethanol after 33 hours, the R-ARSdR strain produced 14.9 g/l ethanol after 33 hours (see FIG. 5B). As such, in the early stage, the ethanol production of the R-ARSdR strain was significantly higher than that of the R-WT strain. However, both the R-WT strain and the R-ARSdR strain produced ethanol to a level near 16.0 g/l after 48 hours. Regarding ethanol yield from the total xylose consumption, the ethanol yield of the R-WT strain was 67% and the ethanol yield of the R-ARSdR strain was 72%. The ethanol yield of the R-ARSdR strain was higher than that of the R-WT strain. Meanwhile in YPDX media, both the R-WT strain and the R-ARSdR strain consumed glucose completely within 9 hours (see FIG. 5C). The glucose consumption rate of the R-WT strain and that of the R-ARSdR strain were each significantly higher than those of experimental yeast strains (the D-WT strain, the D-ARSdR strain, the N-WT strain, and the N-ARSdR strain) (FIG. 4C was compared with FIG. 5C). Also, whereas the R-WT strain consumed 96% of the total xylose after 24 hours, the R-ARSdR strain consumed 92% of the total xylose after 72 hours. The xylose consumption rate of the R-WT strain was slightly higher than that of the R-ARSdR strain (see FIG. 5C). Both the R-WT strain and the R-ARSdR strain almost completely consumed xylose within 32 hours. As such, the xylose consumption rate of the R-WT strain and that of the R-ARSdR strain could be confirmed to tend to increase in the presence of glucose (YPDX media) than in media containing xylose alone (YPX medium). The xylose consumption rate of particularly the R-WT strain was significantly increased (FIG. 5A was compared with C). The result is in contrast to that of experimental yeast strains (the D-WT strain, the D-ARSdR strain, the N-WT strain, and the N-ARSdR strain). It was suggested that the R-WT strain and the R-ARSdR strain that are industrial strains are more appropriate for fermentation of a saccharified solution (comprising mixed sugar composition containing glucose and xylose) from wood-based biomass. In YPDX media, regarding ethanol production rate, difference in ethanol production rate between the R-WT strain and the R-ARSdR strain was decreased in a manner similar to the case of xylose consumption rate, but the ethanol production rate of the N-WT strain was slightly higher than that of the R-ARSdR strain (FIG. 5B was compared with D). Specifically, in YPDX media, whereas the R-WT strain produced 35.3 g/l ethanol after 24 hours, the R-ARSdR strain produced 33.7 g/l ethanol after 24 hours. Both the R-WT strain and the R-ARSdR strain produced ethanol to a level near 36.0 g/l after 32 hours (see FIG. 5D). Regarding ethanol yield from the total sugar (glucose+xylose) consumption, the ethanol yield of the R-WT strain was 82% and the ethanol yield of the R-ARSdR strain was 76%. The ethanol yield of the R-WT strain was slightly higher than that of the R-ARSdR strain. The reason why the xylose consumption rate, the ethanol production rate, and the ethanol yield of the R-WT strain were slightly better than those of the R-ARSdR strain in YPDX media is unclear. It is suggested that this may be due to relatively low $NADP^+$-dependent activity in the R-ARSdR strain (see FIG. 3). Similar to the results in FIG. 4, ethanol yield was higher in YPDX media than in YPX media. Further surprisingly, similar to the results in FIG. 4, although the xylose consumption rate was lower than the glucose consumption rate, xylose was consumed even during glucose consumption (0 to 9 hours) (see FIG. 5C), suggesting almost no effects of glucose suppression. Moreover, xylose fermentation by the R-WT strain and that by the R-ARSdR strain proceeded at rates higher than those of experimental yeast strains (the D-WT strain, the D-ARSdR strain, the N-WT strain, and the N-ARSdR strain). It is suggested that this may be because glucose fermentation by the R-WT strain and the R-ARSdR strain proceeded at rates higher than the experimental yeast strains. Similar results were obtained for the T-WT strain and the T-ARSdR strain. Also in YPX media, the xylose consumption rate, the ethanol production rate, and the ethanol yield of the T-WT strain were higher than those of the T-ARSdR strain. It is suggested that this may be due to low $NADP^+$-dependent activity in the T-ARSdR strain (see FIG. 3). In any event, it was suggested that glucose xylose co-fermentation by genetic recombinant yeast having xylose fermentability provided thereto, which is an object over the years for industrialization, can be realized through the use of these yeast strains.

Figure 6:
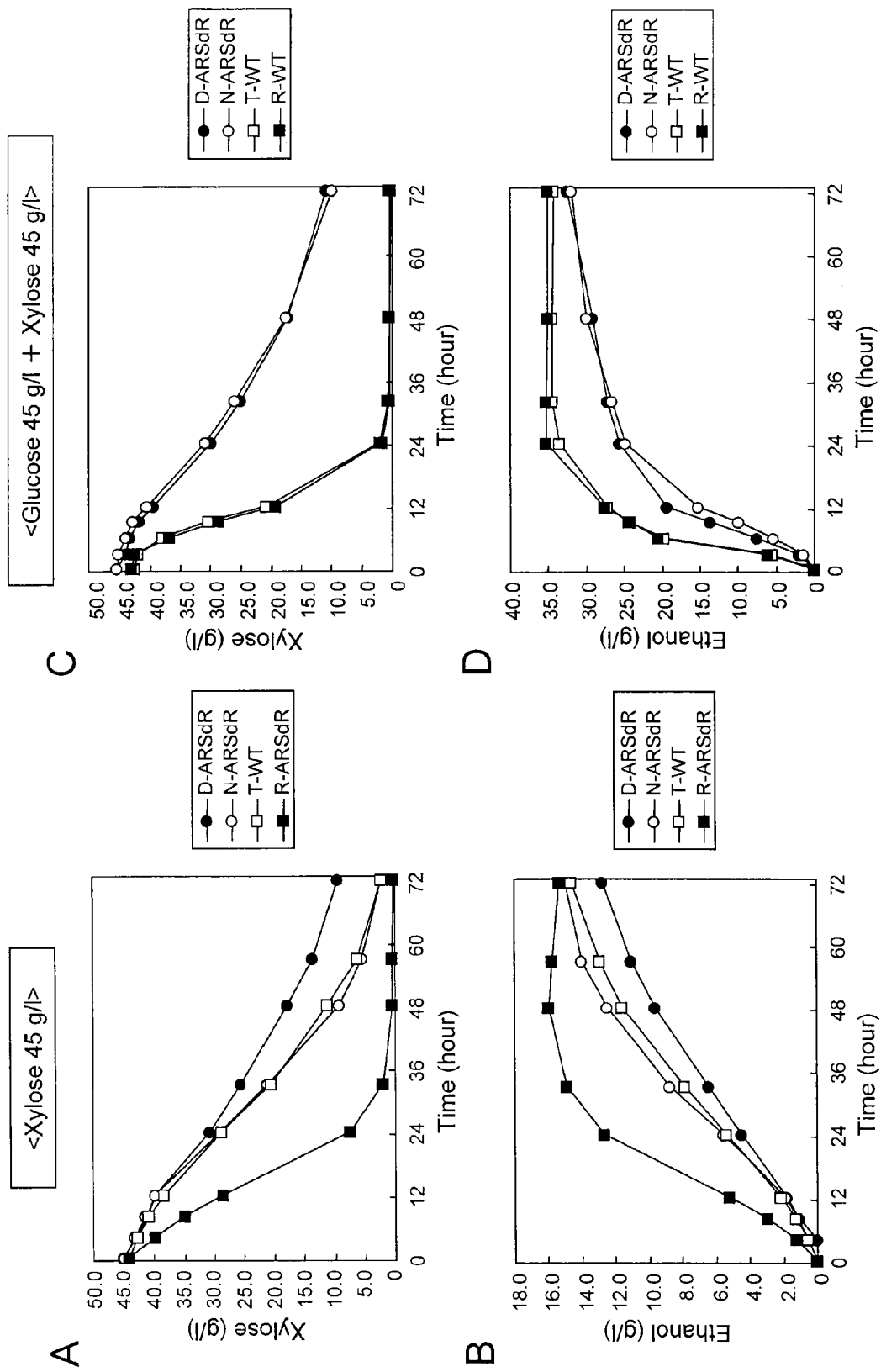
FIG. 6 shows the anaerobic ethanol fermentability (xylose consumption and ethanol production in YPX media and YPDX media) of genetic recombinant yeast strains (the D-ARSdR strain, the N-ARSdR strain, the T-WT strain, and the R-ARSdR strain in the case of YPX media; and the D-ARSdR strain, the N-ARSdR strain, the T-WT strain, and the R-WT strain in the case of YPDX media) having higher xylose fermentability as a result of comparing the WT strains with the ARSdR strains (from each host yeast strain).

FIG. 6 shows the xylose consumption (see FIG. 6A) and the ethanol production (see FIG. 6B) with time of the D-ARSdR strain, the N-ARSdR strain, the T-WT strain, and the R-ARSdR strain and the xylose consumption (see FIG. 6C) and the ethanol production (see FIG. 6D) with time of the D-ARSdR strain, the N-ARSdR strain, the T-WT strain, and the R-WT strain as a result of anaerobic culture in media containing xylose alone (YPX media) (see FIGS. 6A and B) and mixed sugar media containing glucose and xylose (YPDX media) (see FIGS. 6C and D). Comparison was made between the WT strain and the ARSdR strain using each host yeast in YPX media and in YPDX media. Thus, yeast strains with better xylose fermentability (e.g., xylose consumption rate, ethanol production rate, and ethanol yield) were selected. Specifically, in the case of YPX media, the D-ARSdR strain was selected when a host yeast strain was the D452-2 strain, the N-ARSdR strain was selected when the same was the INVSc1 strain, the T-WT strain was selected when the same was the Type-II strain, and the R-ARSdR strain was selected when the same was the IR-2 strain. Also in the case of YPDX media, the D-ARSdR strain was selected when a host yeast strain was the D452-2 strain, the N-ARSdR strain was selected when the same was the INVSc1 strain, the T-WT strain was selected when the same was the Type-II strain, and the R-WT strain was selected when the same was the IR-2 strain. Through comparison of these yeast strains in terms of xylose consumption and ethanol production, a yeast strain with the highest xylose to ethanol fermentability in YPX media and the same in YPDX media were examined. In YPX media, a yeast strain with the highest xylose consumption rate and the highest ethanol production rate was the R-ARSdR strain, followed by the N-ARSdR strain and the T-WT strain, while both rates were somewhat lower in the D-ARSdR strain (see FIGS. 6A and B). Whereas the R-ARSdR strain consumed 96% of the total xylose after 33 hours, both the N-ARSdR strain and the T-WT strain consumed 95% of the total xylose after 72 hours. The D-ARSdR strain consumed 79% of the total xylose after 72 hours (see FIG. 6A). Compared with other yeast strains, the xylose consumption rate of the R-ARSdR strain was significantly higher and consumed almost completely xylose within 48 hours. Moreover, in YPX media, whereas the R-ARSdR strain produced 14.9 g/l ethanol after 33 hours, both the N-ARSdR strain and the T-WT strain produced 14.8 g/l ethanol after 72 hours, and then the D-ARSdR strain produced 12.7 g/l ethanol after 72 hours (see FIG. 6B). As such, in the early stage, the ethanol production of the R-ARSdR strain was significantly higher than that of other yeast strains, but both the N-ARSdR strain and the T-WT strain could produce ethanol to a level similar to that of the R-ARSdR strain after 72 hours. Regarding ethanol yield from the total xylose consumption, the ethanol yield of the R-ARSdR strain was 72%, the ethanol yield of the N-ARSdR strain and that of the T-WT strain were both 69%, and the ethanol yield of the D-ARSdR strain was 70%. The ethanol yield of the R-ARSdR strain was the highest. Also regarding ethanol yield, the ethanol yield of the D-ARSdR strain was the second highest following that of the R-ARSdR strain. Meanwhile, in YPDX media, both the T-WT strain and the R-WT strain completely consumed glucose within 9 hours, while both the D-ARSdR strain and the N-ARSdR strain completely consumed glucose within 24 hours. Also in YPDX media, strains with the highest xylose consumption rate and the highest ethanol production rate were the R-WT strain and the T-WT strain. The xylose consumption rate and the ethanol production rate of the D-ARSdR strain and the N-ARSdR strain were lower than them (see FIGS. 6C and D). Whereas both the R-WT strain and the T-WT strain consumed 96% of the total xylose after 24 hours, the D-ARSdR strain and the N-ARSdR strain consumed 78% and 76%, respectively, of the total xylose after 72 hours (see FIG. 6C). Compared with the D-ARSdR strain and the N-ARSdR strain, the xylose consumption rate of the R-WT strain and the same of the T-WT strain were significantly higher and almost completely consumed xylose within 32 hours. Furthermore, in YPDX media, whereas the R-WT strain and the T-WT strain produced 35.3 g/l ethanol and 33.5 g/l ethanol, respectively, after 24 hours, the D-ARSdR strain and the N-ARSdR strain produced 32.5 g/l ethanol and 32.0 g/l ethanol, respectively, after 72 hours (see FIG. 6D). As such, in the early stage, the ethanol production of the R-WT strain and the same of the T-WT strain were significantly higher than the D-ARSdR strain and the N-ARSdR strain. Both the D-ARSdR strain and the N-ARSdR strain could produce ethanol to levels similar to those of the R-WT strain and the T-WT strain after 72 hours. Regarding ethanol yield from the total xylose consumption, the ethanol yield of the R-WT strain was 82%, the ethanol yield of the D-ARSdR strain and the ethanol yield of the T-WT strain were both 80%, and the ethanol yield of the N-ARSdR strain was 77%. The ethanol yield of the R-WT strain was the highest. The above results revealed that in media containing xylose alone (YPX media), the R-ARSdR strain was the best yeast strain in terms of xylose to ethanol fermentability (e.g., xylose consumption rate, ethanol production rate, and ethanol yield). Meanwhile, in the presence of glucose (YPDX media), the R-WT strain was the best yeast strain in terms of xylose to ethanol fermentability. It was revealed that the T-WT strain was also excellent in xylose consumption rate and ethanol production rate.

Figure 7:
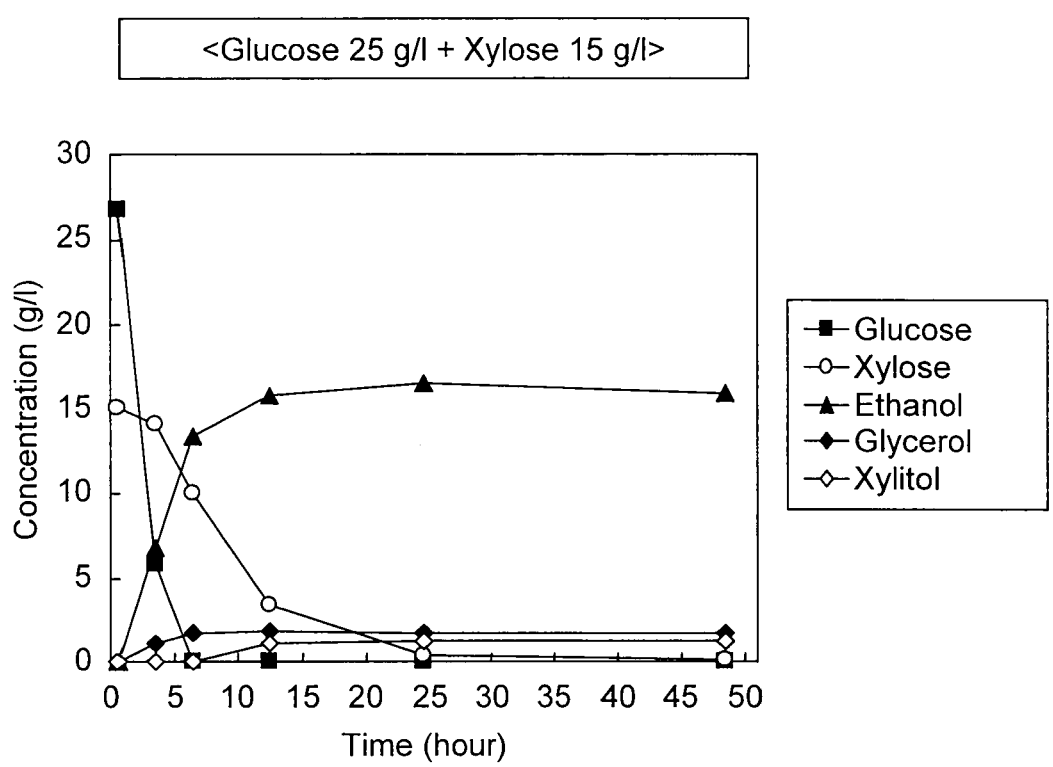
FIG. 7 shows the anaerobic ethanol fermentability (glucose and xylose consumption and ethanol, glycerol, and xylitol production in YPDX2 media) of a genetic recombinant yeast strain (the R-WT strain) prepared using the IR-2 strain as a host yeast.

Dr. Ho et al. of Purdue University have obtained ethanol in high yields from xylose in the presence of glucose using the Saccharomyces yeast 424A (LNH-ST) strain capable of producing ethanol in high yields from xylose. As a result of this Example, the R-WT strain was found to have the highest xylose fermentability in the presence of glucose. This yeast strain was compared with the 424A (LNH-ST) strain of the Dr. Ho et al in terms of xylose fermentability. For this purpose, the R-WT strain was anaerobically cultured in a complete medium (YPDX2 medium) with sugar composition (25.0 g/l glucose and 15.0 g/l xylose) almost the same as that in the fermentation experiment conducted by Dr. Ho et al., and then xylose fermentability was examined (see FIG. 7). According to Dr. Ho et al., mixed sugar containing 25.5 g/l glucose and 17.0 g/l xylose was fermented using the 424A (LNH-ST) strain. Thus, glucose was completely consumed within 3 hours and 80% of the total xylose was consumed after 48 hours. As a result, 15.1 g/l ethanol was produced after 48 hours and the ethanol yield from the total sugar consumption was 75.7%. Also, glycerol, which is an intermediate metabolite, was produced in a small amount, but almost no acetic acid was produced and xylitol was never produced at all. R-WT was examined, as in FIG. 7. Glucose was completely consumed within 6 hours. The time taken for this consumption has a little longer than that taken by the 424A (LNH-ST) strain, but most xylose (98% of the total xylose) was consumed after 24 hours, which was a half of the time taken by the 424A (LNH-ST) strain. As a result, 16.5 g/l ethanol was produced after 24 hours and the ethanol yield from the total sugar consumption reached 77.9%. (The ethanol yield from the total xylose consumption was 76.1%.) Also, glycerol and xylitol, which are intermediate metabolites, were produced in small amounts (1.7 g/l or less), but almost no acetic acid was produced. Therefore, it was suggested that the R-WT strain is superior to the 424A (LNH-ST) strain, which is a recombinant yeast strain reported to have the best xylose fermentability with regard to all factors including xylose consumption rate, ethanol production rate, and ethanol yield. That is, it was suggested that the R-WT strain has markedly better xylose fermentability in the presence of glucose than that of the xylose-fermenting yeast strains reported so far.

The above results demonstrated that ethanol can be highly efficiently produced from xylose with the use of the genetic recombinant yeast according to the present invention. In particular, the R-ARSdR strain is a yeast having markedly better xylose fermentability (fermentability of sugar containing xylose alone) than that of the xylose-fermenting yeast reported so far. Furthermore, the R-WT strain is a yeast having markedly better xylose fermentability in the presence of glucose than that of the xylose-fermenting yeast reported so far. The R-ARSdR strain and the T-WT strain also have markedly better xylose fermentability in the presence of glucose than that of the recombinant yeast reported so far, but such fermentability is slightly inferior to that of the R-WT strain.

Hence, the xylose fermentability (see FIG. 5, FIG. 6, and FIG. 7) of the R-ARSdR strain and that of the R-WT strain of the present invention were compared with the xylose fermentability of genetic recombinant yeast and genetic recombinant microorganisms (Escherichia coli, Zymomonas, and Zymobacter) reported to have been provided with xylose fermentability (see FIG. 8). In addition, although ethanol production from xylose with the use of various recombinant microorganisms has been reported, simple comparison of the results is difficult, since medium compositions, sugar compositions, amounts of microorganisms introduced, and the like are different. However, yeast strains with relatively good xylose to ethanol conversion efficiency were picked up as in FIG. 8 based only on the results of a batch fermentation experiment using xylose and mixed sugar containing xylose. As a result, it was suggested that the R-ARSdR strain and the R-WT strain of the present invention had xylose fermentability at the same or higher levels than known good xylose-fermenting yeast•microorganisms. Specifically, the R-ARSdR strain exhibited the highest rate of fermenting ethanol from xylose in media containing xylose alone. Also, the xylose-to-ethanol yield of the R-WT strain was relatively high in the presence of glucose, and the xylose fermentation rate thereof was the highest. In addition, no results for the T-WT strain are described herein. It is reported that the xylose fermentability (and particularly, the fermentation rate) of the T-WT strain was greater than that of any xylose-fermenting yeast•microorganisms, as in FIG. 8, although the xylose fermentability thereof was less than that of the R-WT strain.

Figure 9:
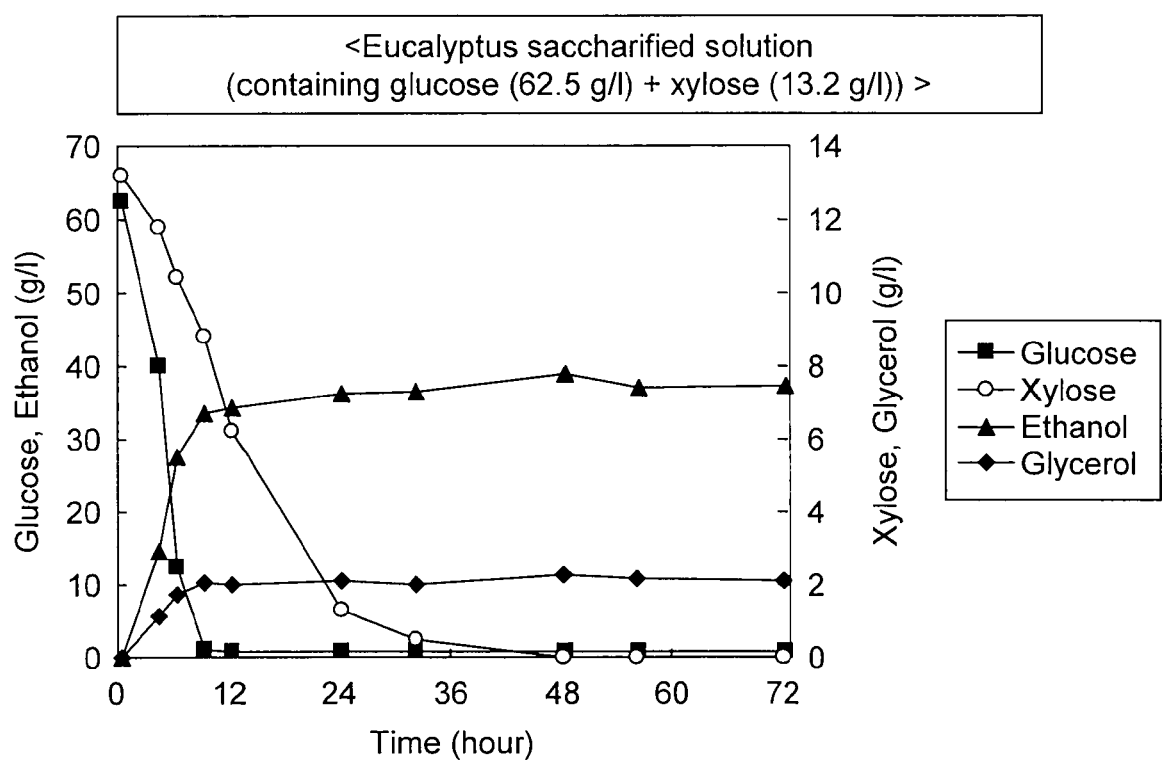
FIG. 9 shows the anaerobic ethanol fermentability (glucose and xylose consumption and ethanol and glycerol production in a saccharified solution prepared from eucalyptus) of a genetic recombinant yeast strain (the R-WT strain) prepared using the IR-2 strain as a host yeast.

Next, the efficiency of the genetic recombinant yeast of the present invention to produce ethanol from glucose or xylose contained in a saccharified solution prepared from lignocellulose-based biomass was examined. A saccharified solution prepared from eucalyptus that is a broad-leaved tree was fermented using the R-WT strain exerting the best fermentability in the above fermentation experiment using the mixed sugar. The eucalyptus saccharified solution was prepared as follows: eucalyptus wood chips (provided by Oji Paper Group) were milled with a ball mill (BM) and then 100 ml of a solution prepared by adding an enzyme cocktail (40 FPU/g substrate) to 50 mM acetate buffer (pH5.0) was added to 20 g of pre-treated wood powders. The thus obtained saccharified solution was adjusted at pH 5.5 using NaOH and then 1% yeast extract was added. The sugar composition of the eucalyptus saccharified solution was examined by HPLC analysis. The eucalyptus saccharified solution contained 62.5 g/l glucose, 1.1 g/l mannose, 1.2 g/l galactose, 13.2 g/l xylose, and 0.7 g/l arabinose. The anaerobic fermentability of the R-WT strain in the eucalyptus saccharified solution was then examined. The R-WT strain consumed glucose almost completely within 9 hours and completely consumed xylose after 48 hours (see FIG. 9). Also, the R-WT strain completely consumed mannose within 4 hours, completely consumed galactose within 24 hours, and further surprisingly, completely consumed arabinose within 48 hours (not shown). As a result, 38.9 g/l ethanol was produced after 48 hours and the ethanol yield from the total sugar consumption reached a level as high as 97.6%. This yield was significantly higher than ethanol yield obtained from single (i.e., xylose alone) sugar or mixed sugar containing glucose and xylose in the above synthetic medium. It was revealed that the yeast strain of the present invention can also be used for fermentation of such saccharified solution prepared from lignocellulose-based biomass and is applicable at the practical level. In addition, glycerol, which is an intermediate metabolite, was produced in a small amount mainly upon glucose fermentation (2.3 g/l or less), but almost no xylitol was produced. Furthermore, similar to the results (FIGS. 4-7) of the fermentation experiments for mixed sugar in the above synthetic media, whereas the xylose consumption rate was lower than the glucose consumption rate, xylose was consumed even during glucose consumption (0-9 hours), suggesting almost no effects from glucose suppression. It was revealed through these results that the genetic recombinant yeast (the R-WT strain) of the present invention can efficiently ferment not only xylose or mixed sugar containing glucose and xylose in synthetic media, but also sugar such as glucose or xylose contained in a saccharified solution prepared from lignocellulose-based biomass.

Example 13

Further Improvement in Xylose Fermentability

Figure 10:
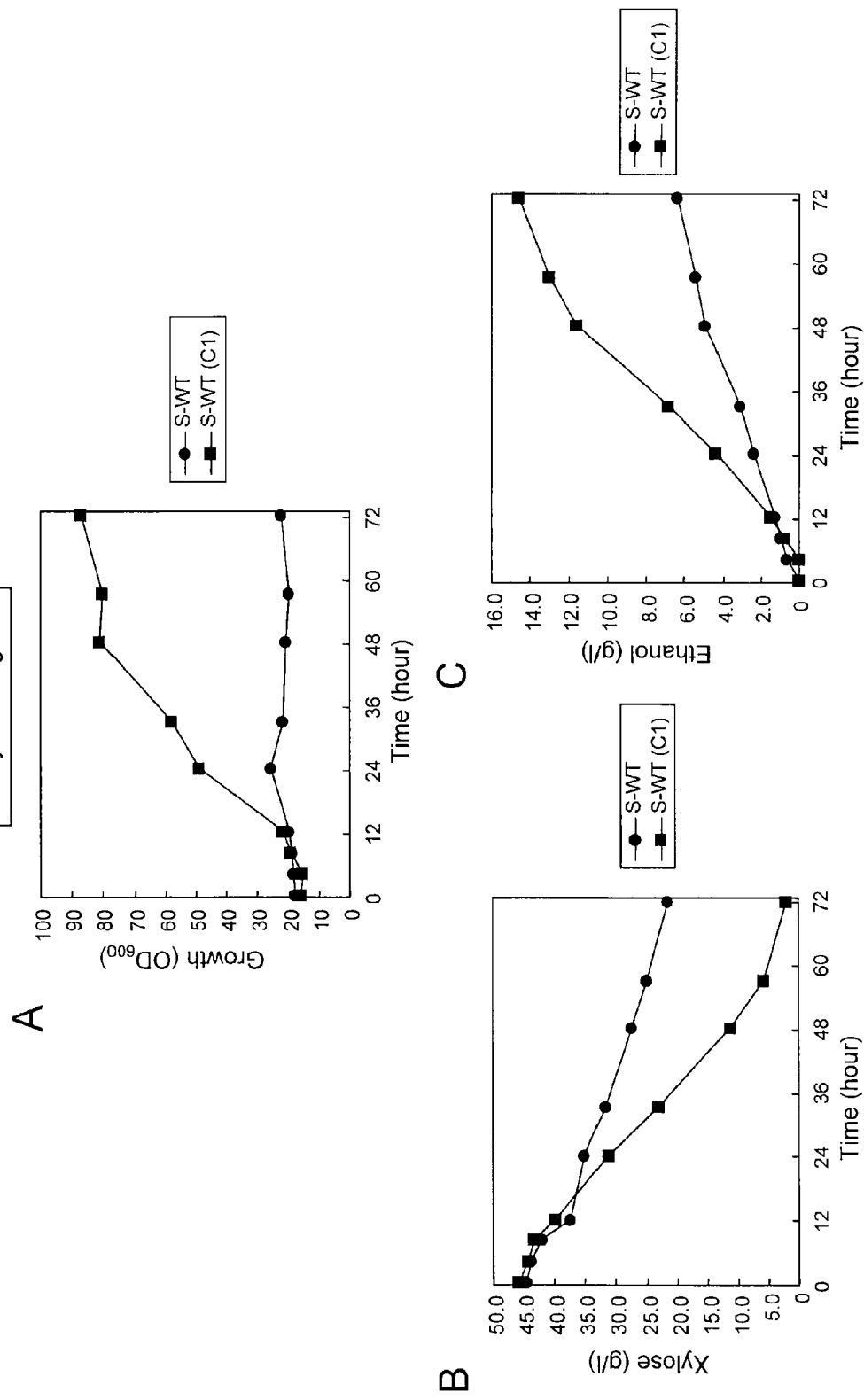
FIG. 10 shows the anaerobic ethanol fermentability (growth, xylose consumption, and ethanol production in YPX media) of a genetic recombinant yeast strain (the S-WT strain) prepared using the shochu yeast No. 3 strain (Sake yeast kyokai No. 3) as a host yeast and an S-WT (C1) strain obtained by subjecting the S-WT strain to acclimatization treatment.

The pAURXKXDH (WT) XR plasmid prepared in Example 7 was introduced into the shochu yeast No. 3 strain (Sake yeast kyokai No. 3) that is a practical strain, so as to prepare an S-WT strain. Then the activity of XR, that of XDH, and that of XK were determined. As a result, expression at levels almost equivalent to those in the T-WT strain and the R-WT strain was confirmed. Next, an experiment for anaerobic ethanol fermentation from xylose was conducted. Fermentability in the presence of glucose and xylose (YPDX media) was almost the same as that in Type-II. However, in media containing xylose alone (YPX media), almost no growth of the S-WT strain was observed (see FIG. 10A). Moreover, the S-WT strain consumed almost no xylose (see FIG. 10B), so that the ethanol production was less than those of the above-mentioned other genetic recombinant yeast strains (see FIG. 10C). In YPX media, the S-WT strain consumed only 52% of the total xylose after 72 hours, so that the xylose consumption rate was lower than the D-WT strain or the N-WT strain, which is an experimental strain (see FIG. 4A). Moreover, in YPX media, the S-WT strain produced only 6.3 g/l ethanol after 72 hours, so that the ethanol production rate was lower than that of the D-WT strain or the N-WT strain, which is an experimental strain (see FIG. 4B). The ethanol yield of the S-WT strain from the total xylose consumption was 54% that was lower than those of the above other genetic recombinant yeast strains. The reason for the low level of xylose fermentability of the S-WT strain in YPX media has not yet been elucidated, but it may be because the xylose fermentability of the S-WT strain depends on fermentability of the host shochu yeast No. 3 strain.

To improve the lower level of xylose fermentability of the S-WT strain compared with other genetic recombinant yeast strains, the S-WT strain was subjected to acclimatization treatment through subculture thereof via application of selection pressure thereto to make the S-WT strain adaptable to an environment in which xylose fermentation can be performed. The S-WT strain was anaerobically cultured in a minimal medium (drop out mix supplemented with 6.7 g/l yeast nitrogen base w/o amino acids, 30 g/l xylose, 1 g/l glucose, and all amino acids (2 g/l): SCDX medium) containing xylose and a small amount of glucose at 30° C. for 72 hours. The two reasons for the addition of glucose to the media are as follows: one reason is that since the expression by a PGK promoter (linked upstream of the 3 types of gene integrated into the chromosome) is accelerated by glucose, xylose metabolism is thought to progress with the addition thereof; and the other reason is that if cells are returned to a medium in the presence of glucose after subculture in a medium containing xylose alone, cells may be affected by glucose suppression, but if glucose is added in advance to the medium, xylose fermentation is thought to be possible almost without the effects by glucose suppression. After 72 hours, a small amount of the S-WT strain extracted from the culture solution was further subcultured in a new SCDX medium and then similarly cultured anaerobically. This was repeated for 10 passages, the S-WT strain obtained after 10 passages was designated an S-WT (C1) strain.

The fermentability of the S-WT (C1) strain in the presence of glucose and xylose (YPDX media) was almost the same as that of the S-WT strain before acclimatization treatment. However, the xylose fermentability of the S-WT(C1) strain in a medium containing xylose alone (YPX media) was confirmed to be significantly improved compared with that of the S-WT strain before acclimatization treatment (see FIG. 10). Specifically, the growth of the S-WT (C1) strain was confirmed in an YPX medium (see FIG. 10A) and the xylose consumption was accelerated compared with the S-WT strain before acclimatization treatment (see FIG. 10B). As a result, ethanol production was significantly increased (see FIG. 10C). In YPX media, the S-WT strain consumed 96% of the total xylose after 72 hours and exerted more accelerated xylose consumption compared with experimental strains, the D-WT strain and the N-WT strain (see FIG. 4A and FIG. 10B). Furthermore, in YPX media, the S-WT(C1) strain produced 14.6 g/l ethanol after 72 hours and the ethanol yield thereof from the total xylose consumption was 65%, demonstrating that the xylose fermentability of the S-WT(C1) strain improved in comparison with the S-WT strain before acclimatization treatment. Also, the S-WT strain was compared with the S-WT (C1) strain in terms of the activity of XR, that of XDH, and that of XK. As a result, somewhat decreased activity was observed overall in the S-WT (C1) strain, but no significant difference was observed. Accordingly, it was inferred that the improved xylose fermentability of the S-WT strain was not due to elevated activity of an xylose metabolic system enzyme after acclimatization treatment, but rather due to a strengthened bypass for xylose metabolism, such as enzyme activity enhanced by introduction of a mutation into a gene involved in xylose incorporation or an enzyme gene in the pentose phosphate pathway downstream of XK.

INDUSTRIAL APPLICABILITY

Through anaerobic culture of the genetic recombinant yeast of the present invention, such yeast can highly efficiently convert xylose to ethanol (the xylose fermentation rate is high and the strain produces ethanol from xylose in high yields), so that highly efficient conversion of xylose contained in wood-based biomass to ethanol, which is expected to serve as next-generation liquid energy source, can be realized. Also, xylose metabolic system (XR, XDH, and XK) genes are all efficiently introduced via chromosomal integration, so that the resultant is very stable and can be directly grown in a saccharified solution without requiring culture in a selective medium. In addition to its inexpensiveness, increased growth rate and increased sugar metabolic rate can be expected. Furthermore, the R-ARSdR strain and the R-WT strain (host yeast: IR-2 strain) with the highest xylose fermentability among the strains of the present invention are aggregating yeast strains. Hence, continuous and repeated fermentation are possible, a high yeast concentration can be maintained by the recylcling of yeast, and higher ethanol productivity can be obtained. Although xylose fermentation is generally suppressed in the presence of glucose, all of the genetic recombinant yeast strains of the present invention can co-ferment xylose simultaneously even in the presence of glucose. In particular, the genetic recombinant yeast strains, the hosts of which are industrial strains (the IR-2 strain and the Type-II strain), have an extremely desirable property such that xylose fermentation is significantly accelerated without delaying xylose fermentation even in the presence of glucose. Thus, ethanol can be highly efficiently produced from a saccharified solution prepared from lignocellulose-based biomass such as woody waste or agricultural waste. Specifically, the genetic recombinant yeast of the present invention is a hexose-pentose cofermenting yeast that addresses the problem of glucose suppression that has inhibited industrialization. The genetic recombinant yeast of the present invention can also be said to be a xylose-fermenting yeast appropriate for long-awaited practical use and industrialization. Furthermore, xylose metabolic system expression cassettes to be used in the present invention can be integrated into the chromosomes of all host yeast strains. Hence, such cassettes can also be integrated into the chromosomes of industrial yeast strains other than IR-2, Type-II, shochu yeast No. 3, and the like shown in the Examples of the present invention. Furthermore, hexose-pentose cofermenting yeast having strong xylose fermentability suitable for industrial use can also be prepared. In addition, the xylose fermentability of a recombinant yeast strain can be improved by a series of acclimatization treatment steps involving performing subculture while applying selection pressure in xylose-containing media.

All publications, patents, and patent applications cited herein are incorporated herein by reference in their entirety.

SEQUENCE LISTING FREE TEXT

SEQ ID NOS: 3-6, 8, 9, 11, and 12 denote synthetic oligonucleotide sequences.

The invention claimed is:

1. A genetic recombinant yeast capable of producing ethanol from xylose, in which a xylose reductase gene, a xylitol dehydrogenase gene, and a xylulokinase gene are introduced by chromosomal integration, wherein the xylose reductase gene, the xylitol dehydrogenase gene, and the xylulokinase gene are each expressed by a PGK promoter which constantly expresses each gene and the genetic recombinant yeast is prepared from strain IR-2 (FERM BP-754).

2. The genetic recombinant yeast according to claim 1, wherein the xylose reductase gene and the xylitol dehydrogenase gene are derived from a yeast.

3. The genetic recombinant yeast according to claim 2, wherein the xylose reductase gene and the xylitol dehydrogenase gene are derived from a yeast selected from the group consisting of *Candida Shehatae, Pichia stipitis*, and *Pachysolen tannophilus*.

4. The genetic recombinant yeast according to claim 3, wherein the xylose reductase gene and the xylitol dehydrogenase gene are derived from *Pichia stipitis*.

5. The genetic recombinant yeast according to claim 1, wherein the xylulokinase gene is derived from a yeast or a bacterium.

6. The genetic recombinant yeast according to claim 5, wherein the xylulokinase gene is derived from a yeast or a bacterium selected from the group consisting of *Candida Shehatae, Pichia stipitis, Pachysolen tannophilus, Saccharomyces cerevisiae, Schizosaccaromyces pombe*, and *Escherichia coli*.

7. The genetic recombinant yeast according to claim 6, wherein the xylulokinase gene is derived from *Saccharomyces cerevisiae*.

8. The genetic recombinant yeast according to claim 1, wherein the xylose reductase gene and the xylitol dehydrogenase gene are derived from *Pichia stipitis* and the xylulokinase gene is derived from *Saccharomyces cerevisiae*.

9. The genetic recombinant yeast according to claim 1, wherein the xylose reductase gene, the xylitol dehydrogenase gene, and the xylulokinase gene are constitutively expressed.

10. The genetic recombinant yeast according to claim 1, wherein the xylitol dehydrogenase gene encodes modified-type xylitol dehydrogenase, DNA disclosed as SEQ ID NO: 1 and protein disclosed as SEQ ID NO: 13, prepared by changing the coenzyme requirement to nicotinamide adenine dinucleotide phosphate (NADP+) requirement.

11. The genetic recombinant yeast according to claim 1, wherein the xylose reductase gene, the xylitol dehydrogenase gene, and the xylulokinase gene are integrated into a single allele of a chromosomal DNA by homologous recombination, or are separately integrated onto different alleles of a chromosomal DNA by homologous recombination.

12. The genetic recombinant yeast according to claim 1, wherein the genetic recombinant yeast is prepared from *Saccharomyces cerevisiae*.

13. A method for obtaining ethanol comprising producing ethanol from xylose, with the genetic recombinant yeast according to claim 1.

14. A method of obtaining ethanol comprising producing ethanol from a saccharified solution prepared from lignocellulose-based biomass with the genetic recombinant yeast according to claim 1.

15. A method for improving the xylose fermentability of the genetic recombinant yeast according to claim 1 by acclimatizing the genetic recombinant yeast.

* * * * *